(12) United States Patent
Daly et al.

(10) Patent No.: US 11,000,780 B1
(45) Date of Patent: May 11, 2021

(54) TORUS REACTOR FOR A COMBINED CELL ISOLATOR AND BIOREACTOR

(71) Applicant: AnuCell Biosystems Limited, Limerick (IE)

(72) Inventors: John Daly, Tipperary (IE); Kieran Curran, Limerick (IE); Macdara Glynn, Galway (IE); Mark McCabe, Dublin (IE); David Merrigan, Clare (IE); Jason Ryan, Tipperary (IE); John P. Griffin, Clare (IE); Caitriona Ryan, Clare (IE); Martin Reddin, Laois (IE)

(73) Assignee: AnuCell Biosystems Limited, Limerick (IE)

( * ) Notice: Subject to any disclaimer, the term of this patent is extended or adjusted under 35 U.S.C. 154(b) by 0 days.

(21) Appl. No.: 16/706,558

(22) Filed: Dec. 6, 2019

(51) Int. Cl.
*B01D 15/18* (2006.01)
*C12N 15/85* (2006.01)
(Continued)

(52) U.S. Cl.
CPC ............ *B01D 15/1892* (2013.01); *B03C 1/01* (2013.01); *B03C 1/30* (2013.01); *C12M 33/14* (2013.01);
(Continued)

(58) Field of Classification Search
CPC ............ B01D 15/1892; B01D 21/0009; B01D 21/26; B01D 21/262; B01D 21/28; B03C 1/30; B03C 1/01; B03C 2201/18; B03C 1/00; B03C 1/02; B03C 1/025; B03C 1/03; B03C 1/32; B03C 2201/22; C12N 15/85; C12N 5/0012; C12N 5/0068;
C12N 13/00; C12N 15/10; C12N 15/1003; C12N 15/1006; C12N 15/101; C12N 15/1013; C12N 15/1017; C12N 2529/00; C12N 2533/30; C12M 41/00; C12M 33/14; C12M 33/00; C12M 35/02; C12M 35/06; C12M 37/02; C12M 45/00; C12M 45/07;
(Continued)

(56) References Cited

U.S. PATENT DOCUMENTS

| 2003/0127396 | A1* | 7/2003 | Siddiqi | ...................... B03C 1/01 210/695 |
| 2008/0008609 | A1* | 1/2008 | Pate | ........................ F04B 17/00 417/415 |

(Continued)

*Primary Examiner* — Joseph W Drodge
(74) *Attorney, Agent, or Firm* — Foley Hoag LLP; Hathaway P. Russell; Stephen J. Kenny

(57) ABSTRACT

Assemblies, systems, and methods for isolation of target material are provided. In various embodiments, an assembly for target material isolation includes a housing having an upper portion and a lower potion together defining an inner chamber. The inner chamber includes a semi-toroidal shape and the semi-toroidal shape defines a longitudinal axis. The assembly further includes one or more fluidic connection from the exterior of the housing to the inner chamber. An isolation material (e.g., polymer wool and/or magnetic beads) may be disposed within the inner chamber. A system includes a configured to fit at least a portion of the housing and releasably couple the assembly. Upon activation of the motor, the assembly may rotate about the longitudinal axis. An angle of the platform may be adjustable to thereby change the angle of the longitudinal axis about which the assembly rotates.

21 Claims, 33 Drawing Sheets

(51) Int. Cl.
*B03C 1/01* (2006.01)
*B03C 1/30* (2006.01)
*C12M 1/26* (2006.01)
*C12M 1/34* (2006.01)

(52) U.S. Cl.
CPC ............. *C12M 41/00* (2013.01); *C12N 15/85* (2013.01); *B03C 2201/18* (2013.01)

(58) Field of Classification Search
CPC ...... C12M 47/02; C12M 47/04; C12M 47/12; C12M 47/18; G01N 1/34; G01N 1/40; G01N 1/4077; G01N 35/0098; G01N 2001/4038; G01N 2035/00564; B01L 3/502; B01L 3/5025; B01L 3/5027; B01L 3/502707; B01L 3/50273; B01L 3/502746; B01L 3/502753; B01L 2300/08; B01L 2300/0861; B01L 2300/0867; B01L 2300/087

USPC ........ 435/173.1, 173.8, 173.9; 210/222, 223, 210/695
See application file for complete search history.

(56) References Cited

U.S. PATENT DOCUMENTS

| | | | |
|---|---|---|---|
| 2012/0115213 A1* | 5/2012 | Hofstadler | B01L 7/52 435/287.2 |
| 2013/0316363 A1* | 11/2013 | Wainwright | B01L 9/52 435/6.15 |
| 2016/0282353 A1* | 9/2016 | Clemens | G01N 33/57492 |
| 2016/0289665 A1* | 10/2016 | Mao | C12N 15/1013 |
| 2017/0336304 A1* | 11/2017 | Wong, Jr. | G01N 1/44 |
| 2018/0028990 A1* | 2/2018 | Frodsham | H01F 7/0231 |
| 2018/0117851 A1* | 5/2018 | Reese | B29C 64/106 |
| 2018/0201984 A1* | 7/2018 | Berry | C12Q 1/6806 |
| 2020/0080998 A1* | 3/2020 | Zhu | G01N 33/54333 |

* cited by examiner

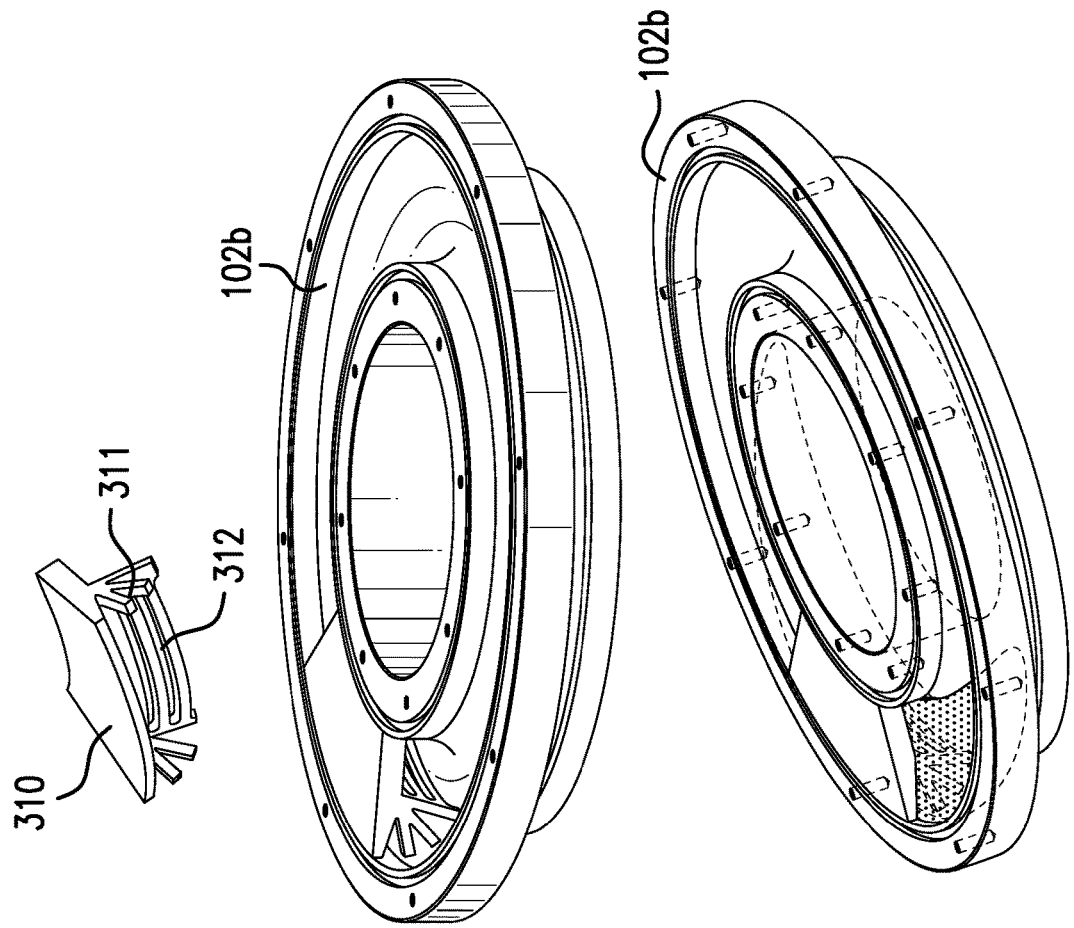
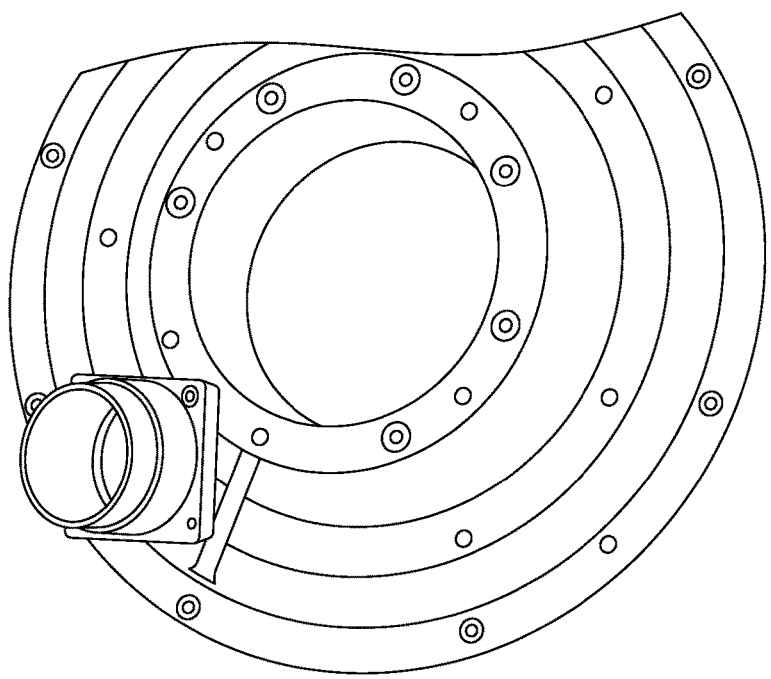
FIG.3A

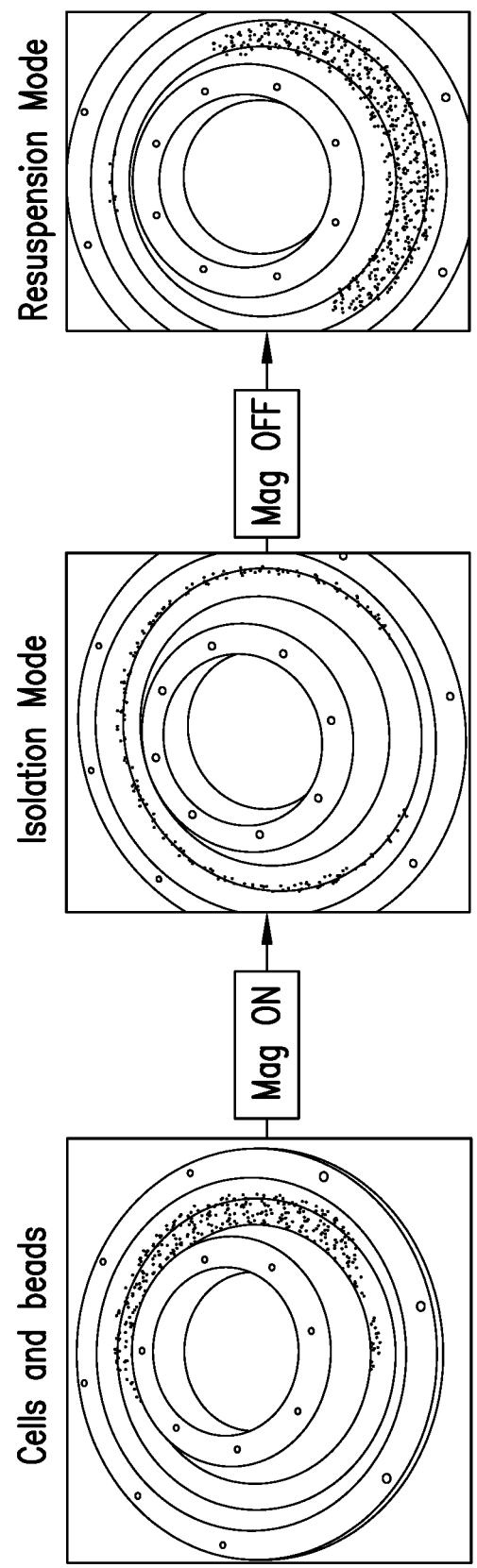

1000

1002 providing an assembly comprising: a housing having an upper portion and a lower potion defining an inner chamber, the inner chamber comprising a semi-toroidal shape, the semi-toroidal shape defining a longitudinal axis; one or more fluidic connections to the inner chamber; and an isolation material disposed within the inner chamber; the isolation material selected from the group consisting of a polymer wool and magnetic particles; and a magnetic ring releasably coupled to the housing, the magnetic ring comprising one or more permanent magnets.

↓

1004 loading a suspension into a fluidic connection, the suspension comprising the target material and the one or more non-target materials.

↓

1006 engaging the assembly with platform, the platform operably coupled to a motor.

↓

1008 activating the motor to rotate the assembly about the longitudinal axis thereby causing either the target material or one or more non-target materials to interact with the isolation material.

↓

1010 extracting either the target material or the one or more non-target mater

TORUS REACTOR FOR A COMBINED CELL ISOLATOR AND BIOREACTOR

BACKGROUND

Embodiments of the present disclosure relate to assemblies, systems, and methods for isolation of target material (e.g., cells) from a suspension of target and non-target materials and subsequent expansion/culture of the isolated target material.

BRIEF SUMMARY

According to embodiments of the present disclosure, assemblies, systems, and methods for isolation of a target material are provided. In various embodiments, an assembly for isolation of target cells and culture of the isolated target cells includes a housing having an upper portion (e.g., a lid) and a lower potion (e.g., a semi-toroidal chamber) together defining an inner chamber. The inner chamber includes a semi-toroidal shape. The semi-toroidal shape defines a longitudinal axis. The housing further includes one or more fluidic connections to the inner chamber and an isolation material is disposed within the inner chamber. The isolation material is selected from a polymer wool and magnetic particles. The assembly further includes a magnetic ring releasably coupled to the housing. The magnetic ring includes one or more permanent magnets.

In various embodiments, a system for isolation of a target material includes an assembly including a housing having an upper portion and a lower potion defining an inner chamber. The inner chamber includes a semi-toroidal shape. The semi-toroidal shape defines a longitudinal axis. The housing further includes one or more fluidic connections to the inner chamber and an isolation material is disposed within the inner chamber. The isolation material is selected from a polymer wool and magnetic particles. The assembly further includes a magnetic ring releasably coupled to the housing. The magnetic ring includes one or more permanent magnets. The system further includes a platform configured to fit at least a portion of the housing thereby releasably coupling the assembly to the platform. The system further includes a motor operably coupled to the platform such that, when the motor is activated, the assembly rotates about the longitudinal axis.

In various embodiments, a method of isolating a target material from one or more non-target materials includes providing an assembly including a housing having an upper portion and a lower potion defining an inner chamber. The inner chamber includes a semi-toroidal shape. The semi-toroidal shape defines a longitudinal axis. The housing further includes one or more fluidic connections to the inner chamber and an isolation material is disposed within the inner chamber. The isolation material is selected from a polymer wool and magnetic particles. The assembly further includes a magnetic ring releasably coupled to the housing. The magnetic ring includes one or more permanent magnets. The method further includes loading a suspension including target mater and one or more non-target materials into a fluidic connection of the housing. The method further includes engaging the assembly with a platform operably coupled to a motor. The method further includes activating the motor to rotate the assembly about the longitudinal axis thereby causing either the target material or one or more non-target materials within the cell suspension to interact with the isolation material. The method further includes extracting either the target materials or the one or more non-target materials from the assembly that did not interact with the isolation material thereby isolating either the target material or non-target materials within the assembly.

BRIEF DESCRIPTION OF THE SEVERAL VIEWS OF THE DRAWINGS

FIGS. 3A-3D illustrate a modular installation (e.g., a frit) disposed within the inner chamber of the assembly according to embodiments of the present disclosure.

FIG. 6 illustrates steps in a process for cell isolation according to embodiments of the present disclosure.

FIG. 10 illustrates a method of isolating target cells and culturing the target cells according to embodiments of the present disclosure.

DETAILED DESCRIPTION

Figure 1A:
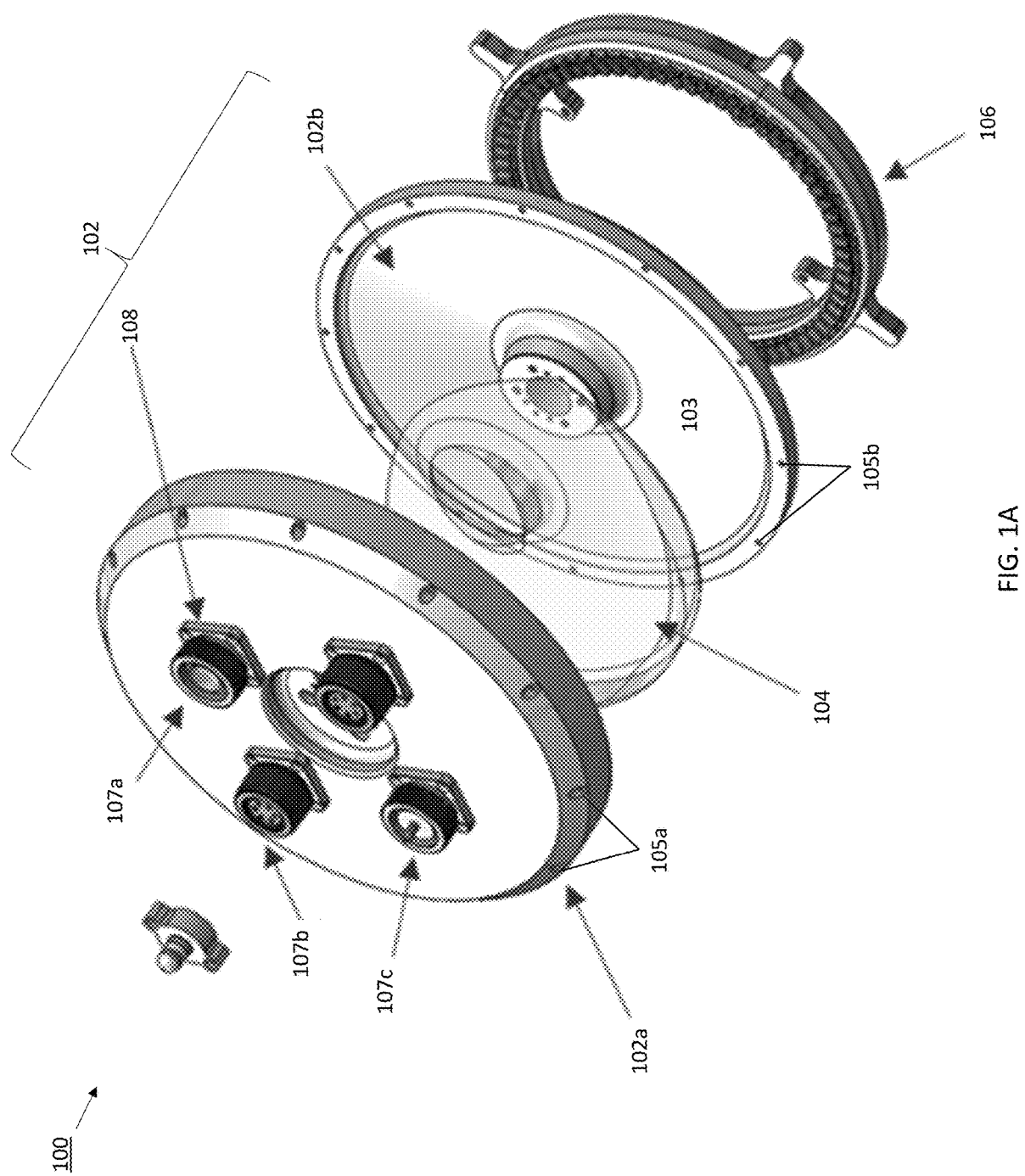
FIG. 1A illustrates an exploded view of an exemplary cell isolation and culture assembly according to embodiments of the present disclosure.

A difficulty with the nascent field of cell manufacture for use in immune-cell therapy is the heavy dependence on manual and/or open systems and protocols to perform all the necessary steps for converting cells (e.g., initial primary PBMC blood cells) to a final cellular product for infusion to a patient. Each step that is open to the atmosphere introduces potential for contamination and/or sample loss, and the cost of such therapies are restrictive based in no small part on the human-hours required for direct interaction with the process.

Currently, the primary method of isolation T-cells from a white blood sample is to incubate the sample with magnetic beads that will attach to the T-cells and allow the isolation of them using magnets. While highly efficient, the beads must be removed further downstream as they cannot be injected into a patient. Furthermore, the beads themselves are highly expensive, even more so when versions must exist that are validated for medical use. Finally, the T-cells that emerge cannot be considered as "untouched"—meaning that the target cells have interacted with an introduced reagent which is not ideal for downstream applications.

Prior art devices that are commercially available for cell isolation and/or cell culture have various disadvantages including having separate devices for each of preparation and processing, requiring transfers which may contaminate a suspension of cells. Moreover, when certain devices are used for a patient, the device cannot be used for any other parallel processing. For some devices, disposable/consumable equipment is expensive and there are also a number of user interactions required for sterile welding. Some prior art devices do not support magnetic-based isolation. Other prior art devices are suitable for cell expansion, but do not provide for cell isolation. Lastly, some prior art devices for cell isolation must be removed later in processing as they cannot be injected into a patient or may interact with the target cells thus potentially affecting the quality of the target cells, making them less desirable for downstream applications.

Accordingly, a need exists for an enclosed and sterile device and system that enables both target cell isolation of a subpopulation of cells from a primary sample and subsequent expansion of the cell numbers by cultural expansion.

Additionally, a need exists to either supplement or re-direct current manufacturing strategies into versions that do not require the need for initial cell isolation using a bead-based reagent.

The assemblies, systems, and methods described herein aim to automate a large part of the process—from initial input (e.g., of initial primary PBMC blood cells) all the way through cell expansion and/or re-formulation of the final product. Quality control may be measured in real-time using on-board sensors, or samples from the product can be sterilely removed from the system for lab based monitoring. Much of the difficulties with cell reactors is the requirement for gas exchange and mixing. These issues may be solved in a small footprint using the rotational effects of the assemblies, systems, and methods described herein. Additionally, the small physical footprint of the torus reactor unit allows for the stacking of a number of individual torus reactors into a secondary instrument that will process each reactor separately allowing parallel processing of a number of doses. The costs may be minimized by using as many external components as possible, with the torus, reagent reservoirs, and tubing being the only disposables. Tubing sets may be minimized as the reagent reservoirs will be directly attached to the torus reactor where possible.

A core principle of the concept is the use of a rotational, enclosed, and sterile chamber to both enable candidate cell isolation of a sub-population of cells from a primary sample, as well as allowing subsequent expansion of the cell numbers by culture expansion—called the "torus reactor." The cell isolation aspect can be mediated by active processes involving an external interaction such as magnetic isolation, or a passive process that can install components within the chamber of the torus that the cell culture will pass through as part of the isolation process, e.g., a polymer based filtration. The chamber may include the internal shape of a torus, but can include features such as baffles, surface re-shaping or various torus geometries to encourage mixing or passage of the culture liquid through a filter-based isolation insert. The chamber unit sits on a 3D rotational platform or chuck that rocks the torus with a defined speed and rotational angle such that the internal fluids travel around the circumference of the torus to optimize mixing, gas exchange and isolation (e.g., magnetic efficiency). The rotational angle and speed can be adjusted in real-time or as part of a program to accommodate the various requirements of the steps of a cell manufacturing strategy. There is a fluidic module that integrates with the torus to allow the addition of reagents necessary for cell manufacture, as well as media exchange and sampling fluidic outputs. Quality control sensors may be integrated to monitor standard cell culture health parameters such as cell number, biomass, viability, oxygen, and carbon dioxide levels.

In various embodiments, components of the assembly and/or system may be made out of any suitable metal, for example, aluminum, steel, and/or titanium. In various embodiments, components of the assembly and/or system may be made out of any suitable polymer, for example, polyethylene, polyurethane, polyethylene terephthalate, polyvinyl chloride, etc. In various embodiments, components of the assembly and/or system may be manufactured by any suitable manufacturing process, such as, for example, injection molding, blow molding, extrusion, thermoforming, vacuum forming, etc. One skilled in the art will recognize that any suitable 3D printing technique may be used to manufacture the components described herein.

The torus reactor assembly is designed to 1) close the entire process of cell manufacture from primary cell (e.g., PBMC) input to product output, 2) maximize the efficiency of the magnetic isolation and/or provide a non-bead-based isolation method for target cell (e.g., T-cells) isolation, and 3) maximize the expansion process for the target cells.

For closing the process, the torus reactor may use the same chamber to isolate the subpopulation of interest, remove the unwanted cells, wash the isolated subpopulation, activate and transduce the cells, expand the cells to a target concentration, wash and re-formulate the isolated cells. If it becomes necessary to expand the internal volume of the torus to accommodate an expanding population, a nested torus architecture can be used where the contents of an initial tours can be transferred to an underlying larger torus using gravity and a "trapdoor" to remove the need for tubing. This will maintain the closed nature of the torus. It will also allow magnetic beads to be separated from the target cells following isolation and remain behind in the first torus.

For magnetic isolation, the torus reactor has an on/off magnetic array positioned outside the internal chamber but distributed around a portion (e.g., 25%-80%) of the circumference of the torus. In various embodiments, the magnetic array is distributed around 80% of the torus reactor. The magnetic array can be dispersed about the torus in a contiguous manner, or include gaps or spaces (of uniform or varying dimension) between adjacent magnets, if so desired. This can be switched on/off by lifting a ring with permanent magnets into a keyed position on the torus and using magnetic proximity for the on condition. Alternatively, permanent magnets can be arranged to produce a Halbach array that will allow the on-off condition to be switched using rotation of the magnets. The Halbach array also has the effect of producing a stronger magnetic field within the torus than what would be achieved by the same magnets arranged in the standard north/south (alternating polarity) orientation. Regardless of the magnetic strategy, when engaged, the magnetic field is distributed over 80% of the circumference of the torus, and is activated concurrently with the rotation of the torus reactor on the 3D platform. For magnetic isolation this has the effect of introducing a lateral displacement of cells relative to the direction of the magnetic field during isolation. This helps overcome one of the problems associated with a pot-magnet approach used by other isolation methods where non-target material is co-isolated as the magnetic material moves en masse to the points of strongest magnetic field in the static pop magnets or permanent magnets used. This has the overall effect of increasing the purity of target population when isolating using the torus reactor. The 20% gap in the magnetic field allows interaction with fluid handling components without risk of scraping or touching the isolated material. Once isolated, the magnetic force is sufficient to overcome the fluidic forces associated with the 3D rotation and so the material can be held in place while fluids are removed/exchanged as required.

In addition to magnetically enabled cell isolation, the torus will allow the integration of any bead-free isolation methods developed that involve the use of polymer wool. In various embodiments, one or numerous frits packed with polymer wool can be placed inside the torus chamber in the liquid path of the culture. The polymer wool will sequester certain cells from a PBMC population while allowing the passage of others. Current data suggests that T-cell and Natural Killer cells (NK) will generally passage through the polymer wool, while monocytes and B-cells will be sequestered. The polymer wool allows the progressive enrichment of T-cells and NK-cells in the liquid culture of the torus, thus enriching the recoverable liquid for these cells. The polymer wool also provides a matrix that can be functionalized to restrict passage of additional cells. In various embodiments, the cells may be treated with reagents that restrict their movement through the polymer wool. For example, if anti-CD56 antibodies are immobilized to the polymer wool, this will restrict the passage of the NK-cells through the polymer wool, increasing the purity of the T-cells.

In various embodiments, the polymer wool may include any suitable polymer material, such as, for example, polyamide, polytetrafluoroethylene (PTFE), polychloroprene, polyimide, polyacrylonitrile, cellulose, copolyamid, polyamide 11 &12, polyethylene terephthalate, etc.

For expansion, the internal chamber of the torus is designed such that the cells are in constant movement due to the 3D rotation. Gas exchange vents are positioned in the roof of the torus reactor may include filters of any suitable size (e.g., 0.22 μm) allowing the exchange of O2 and CO2 between the chamber and environment, but maintaining a sterile inner environment. In various embodiments, a lid of the torus reactor may be made from a gas-exchange friendly material (e.g., a material that naturally allows gases to be exchanged over prolonged period of time without diminishing performance due to condensation or exposure to elevated temperatures). Oxygenation of the culture in encouraged by the 3D rotation coupled with baffles or internal chamber design (e.g., a "twisted torus") that constantly moves cells from the deepest areas of media (which could be oxygen poor) to the upper surfaces of the culture where there is an air interface and oxygen rich. Additionally, the chamber is designed such that no part of the active culture will be more than 1 cm in media depth from the air interface, maximizing oxygenation of the culture. As the torus is constantly rotating in a single direction, this leads to the cells displacing in a single infinite direction. This is distinct from prior art devices where a rocking motion is used to keep the cells mixed and oxygenated. Such rocking, it has been argued, can lead to stress on the cells as they impact the sides of the reactor bag and constantly and sharply change direction. The unidirectional rotation of the torus reactor is designed to minimize such stress. Cellular stress may also be minimized by maintaining a static culture of cells in a high oxygen environment. The caveat of this design is the low capacity of cells per unit volume of media required to operate. The torus reactor will maximize the cell capacity in the available media volume by maintaining high oxygenation but with low stress conditions.

In various embodiments, an assembly for isolation of a target material (e.g., cells, DNA, RNA, etc.) includes a housing having an upper portion and a lower potion together defining an inner chamber. The inner chamber includes a semi-toroidal shape. The housing includes a central hole (e.g., a doughnut hole) defining a longitudinal axis. The assembly further includes one or more opening in the housing fluidly connected to the inner chamber and an isolation material disposed within the inner chamber. In various embodiments, the assembly may be used for culture and/or expansion of the target material.

In various embodiments, the assembly further includes a magnetic ring releasably coupled to the housing. The magnetic ring includes one or more permanent magnets. In various embodiments, the one or more permanent magnets are arranged in a Halbach array. In various embodiments, the magnetic ring extends around about 25% to about 80% of a circumference of the housing. In various embodiments, the magnetic ring extends about the inner circumference of the housing (i.e., the external circumference of the central opening). In various embodiments, the magnetic ring extends about the outer external circumference. In various embodiments, the magnetic ring does not extend around an entire circumference of the housing. In various embodiments, the magnetic ring does not extend around about 10%-75% of the circumference of the housing. In various embodiments, the magnetic ring does not extend around about 20% of the circumference of the housing. In various embodiments, the isolation material includes a plurality of magnetic particles. In various embodiments, the isolation material further includes one or more antibodies, aptamer, ssDNA, RNA, mRNA, etc. configured to selectively bind to a target and to a magnetic particle of the plurality of magnetic particles. In various embodiments, the target may include one or more of: cells, nucleic acids (e.g., DNA, RNA, etc.), enzymes, proteins, antibodies, antigens, etc. In various embodiments, the isolation material comprises a polymer wool. In various embodiments, the polymer comprises a polyamide wool. In various embodiments, the assembly further includes a suspension (e.g., blood sample, a cell suspension, etc.) disposed in the inner chamber. In various embodiments, the suspension may have a plurality of cells disposed within a cell culture media. In various embodiments, the plurality of cells are selected from the group consisting of T cells, B cells, natural killer cells, monocytes, peripheral blood mononuclear cells (PBMCs), apheresis materials, whole blood, and/or a cultured material.

In various embodiments, a depth of the suspension does not exceed about 1 cm to about 10 cm. In various embodiments, a depth of the suspension does not exceed about 1 cm. In various embodiments, the inner chamber is sealed. In various embodiments, the upper portion and the lower portion of the housing are integrally formed (i.e., as a single piece). In various embodiments, the upper portion and the lower portion are made as separate pieces. In various embodiments, the inner chamber has a volume of 1 ml to 1 L. In various embodiments, the inner chamber has a volume of 1 ml to 30 ml. In various embodiments, the housing has a ring torus shape. In various embodiments, the assembly further includes a frit disposed in the inner chamber configured to position material disposed within a fluid. In various embodiments, the frit comprises one or more slits. In various embodiments, the frit comprises one or more arms. In various embodiments, the assembly further includes a second housing having a second inner chamber having a semi-toroidal shape, the first housing being disposed within the second chamber. In various embodiments, the assembly further includes a second housing having a second inner chamber having a semi-toroidal shape, wherein the second housing is adjacent (i.e., external) to the first housing and the second inner chamber is fluidly coupled to the first inner chamber. In various embodiments, the lower portion of the first housing further comprises a trap door configured to allow transfer of contents from the first housing to the second housing. In various embodiments, the assembly further includes a filter disposed within the one or more opening. In various embodiments, the transfer of contents from one assembly to another assembly may be performed via a passive process (e.g., gravity). In various embodiments, the transfer of contents from one assembly to another assembly may be performed via an active process (e.g., creating a pressure differential such as pumping).

In various embodiments, a system for isolation of a target material (e.g., cells, DNA, RNA, etc.) includes an assembly as described above, an end effector configured to interface with the central hole of the housing thereby releasably coupling the assembly to the end effector, and a motor coupled to the end effector such that, when the motor is activated, the assembly rotates about the longitudinal axis. In various embodiments, an angle of the end effector is adjustable. In various embodiments, the system further includes an environmentally-controlled chamber and the assembly is disposed within the environmentally-controlled chamber. In various embodiments, the system may be used for further processing of the target material (e.g., PCR, fragmentation, ligation, cleaving, etc.). In various embodiments, further processing may include culture or expansion of the target material, for example, if the target material includes one or more cells.

In various embodiments, a method of isolating a target material (e.g., cells, DNA, RNA, etc.) from non-target materials within a suspension (e.g., a cell suspension) includes providing an assembly including a housing having an upper portion and a lower potion defining an inner chamber. The inner chamber has a semi-toroidal shape. The housing may include a central hole (e.g., doughnut hole) defining a longitudinal axis. The assembly further includes one or more opening in the housing fluidly connected to the inner chamber and an isolation material disposed within the inner chamber. The method further includes loading a suspension (e.g., cell suspension) into the opening of the housing. The suspension may include one or more target materials and one or more non-target materials. The method further includes engaging the assembly with an end effector operably coupled to a motor. The method further includes activating the motor to rotate the assembly about the longitudinal axis thereby causing the target material within the suspension to interact with the isolation material. The method further includes extracting the non-target material/cells from the assembly thereby isolating the target cells within the assembly (positive isolation). In various embodiments, the non-target material may interact with (e.g., be irreversibly bound to) the isolation material (e.g., polymer wool) and the target material may be extracted from the assembly (negative isolation). In various embodiments, the method includes adjusting an angle of the end effector. In various embodiments, the assembly is rotated at a speed of up to 120 Hz. In various embodiments, the assembly is not rotated at all. In various embodiments, the assembly may be intermittently rotated, about one or a plurality of axes, and stopped. In various embodiments, the method further includes releasably coupling a magnetic ring to the housing, the magnetic ring comprising one or more permanent magnets. In various embodiments, the target material may include one or more of the following: T cells, B cells, natural killer cells, monocytes, peripheral blood mononuclear cells (PBMCs), apheresis materials, whole blood, and/or a cultured material. In various embodiments, the target material may include one or more of the following: DNA, RNA, enzymes, proteins, and antigens, etc. In various embodiments, the method further includes washing the target material(s). In various embodiments, the method further includes processing of the target material(s). For example, when the target material includes cells, activating and transducing the target cells may be performed after washing. For other target materials, processing of the target material(s) may include PCR, ligation, fragmentation, enzymatic, lysing, etc. In various embodiments, the method further includes expanding the target cells to a predetermined concentration after activating and transducing the target cells. In various embodiments, expanding the target cells comprises supplying one or more gases to the inner chamber via one of the one or more openings. In various embodiments, the one or more gases comprises carbon dioxide. In various embodiments, expanding the target cells further comprises activating the motor to rotate the assembly about the longitudinal axis after target cell isolation. In various embodiments, the assembly is rotated in a single direction to thereby minimize cellular stress on the target cells.

In various embodiments, the torus assembly rotation system is designed to produce the smallest and most compact footprint and height as is possible. In various embodiments, it is designed to fit into a single shelf of a standard cell culture incubator. In various embodiments, the void space at the center of the torus will be used to house the motor and other mechanics of the rotator, thus saving space. In various embodiments, a 3D movement device is provided as a two-part instrument. In various embodiments, a docking station may provide all the programming and user interaction required to set the speeds, angle, etc. of the 3D movement device. In various embodiments, the 3D rotation itself will be provided by the second part of the two-part instrument which will interface with the torus ("the rotation system"). In various embodiments, the rotation system can sit on the docking station and have the experimental parameters uploaded. In various embodiments, the rotation system can be transferred to the incubator with a single program uploaded, and the program can then be initiated by the push of a single button when the torus is installed on the rotator. In various embodiments, this process may minimize the requirements for user-interaction components on the rotator, thus making it as small as possible. In various embodiments, the rotation system may be powered by AC being provided into the incubator. In various embodiments, the rotation system may be powered by an on-board battery that can be charged from the docking station, e.g., to allow wireless operation of the rotator. In various embodiments, the docking station and rotation system can both be placed in the incubator for longer incubations where a battery charge will not be sufficient to complete the run (so the device can be powered from the AC supplied to the docking station).

FIG. 1A illustrates an exploded view of an exemplary target cell isolation and target cell expansion assembly 100 according to embodiments of the present disclosure. The assembly 100 includes a housing 102 having an upper portion 102 and a lower potion 102b. When assembled together, the upper and lower portions 102a, 102b define an inner chamber 103 that has a toroidal shape. In various embodiments, the upper and lower portions 102a, 102b are formed as an integral piece (i.e., a single piece). In various embodiments, the upper and lower portions 102a, 102b are formed as separated pieces (as shown in FIG. 1A). In various embodiments, the toroidal shape is a ring toroid. The upper portion 102a and the lower portion 102b may be secured to one another via fixation mechanisms (e.g., screws) placed in fixation holes 105a, 105b. In various embodiments, the upper portion 102a and lower portion 102b include a gasket (e.g. silicone or rubber) between the two components to ensure that a sealed environment is created (and a sterile environment is maintained) in the inner chamber 103.

A cell suspension 104 may be introduced into the inner chamber 103 via one of a plurality of openings/ports 107a-107c in the housing 102. In various embodiments, the openings/ports 107a-107c are located on the top surface of the upper portion 102a. In various embodiments, one or more of the openings/ports 107a-107c may include a cap. In various embodiments, the cap may be suitable for sterile spiking of the cells into the inner chamber using industry-standard sterile spiking methods. In various embodiments, the cap may be a fluidics cap providing an interface for tubing such that fluid (e.g., a washing fluid, cell culture media, etc.) may be introduced into the inner chamber 103. In various embodiments, the cap may be a seal cap that seals the opening/port from the outside atmosphere. In various embodiments, the cap may be a filter cap that allows some exposure to the outside atmosphere. For example, the filter cap may include a 0.22 µm filter that may allow the passage of some molecules (e.g., $O_2$, $N_2$, and/or $CO_2$), but not allow other molecules, particles, and/or microorganisms to pass through. In various embodiments, the openings/ports may be gas exchange vents, and/or permeable membranes.

In various embodiments, the suspension may include a primary source of blood material. For example, the suspension may include one or more of: T cells, B cells, natural killer cells, whole blood, peripheral blood mononuclear cells (PBMCs), leukopaks, apheresis products, and monocytes. In various embodiments, the cells may be suspended in a cell culture media as is known in the art. In various embodiments, a depth of the cell media may not exceed a predetermined height. In various embodiments, the predetermined height may be between 0.1 cm and 10 cm. In various embodiments, the predetermined height may be 1 cm, 2 cm, 3 cm, 4 cm, 5 cm, 6 cm, 7 cm, 8 cm, 9 cm, 10 cm, or any suitable intermediate value in between these values.

The assembly 100 further includes a magnetic ring 106 that may be releasably coupled to the bottom surface of the lower portion 102b of the housing 102. In various embodiments, the housing 102 (e.g. the lower portion) may include one or more keyed portions that are configured to orient the magnetic ring and/or releasably attach the magnetic ring 106 to the housing 102. In various embodiments, the magnetic ring 106 is configured to produce a magnetic field that covers about 80% of the circumference of the housing 102, such that about 20% of the housing is either not exposed to a magnetic field or the magnetic field is weaker (e.g., negligible) in that portion. In various embodiments, the magnetic ring 106 is configured to produce a magnetic field that covers the entire circumference of the housing 102.

In various embodiments, the proportion of the torus circumference that is covered by a magnetic field may be dependent on the interaction of the fluidic-control aspects of the invention with isolated magnetic material. In various embodiments, the maximum coverage of magnetic arc is beneficial (as it allows more efficient washing of the captured material due to less packing at each magnetic locus). In various embodiments, the angle of the magnets may be adjusted such that the volume of the liquid relative to the point of maximum strength magnetic field. In various embodiments, if the fluid level is such that the magnets are positioned too high, the angle of the rotation may be increased or the magnets may be positioned lower in the torus sidewall. In various embodiments, different volume tori may include different positioning of the magnets (and rotational angle) such that each volume of torus reactor is optimized to ensure maximum efficiency of the magnetic field specific to the volume.

In various embodiments, the assembly 100 further includes an isolation material disposed in the inner chamber 103. The isolation material may be configured to isolate target cells (e.g., a specific type) from other cells in a cell suspension. In various embodiments, the isolation material may include magnetic particles, as are known in the art. In various embodiments, magnetic particles (e.g., beads) may mediate binding to a target material by an antibody interaction, or other interactions for example the charge/crowding interaction that mediates the Solid Phase Reversible Immobilization (SPRI) capture of DNA. In various embodiments, where the target material includes nucleic acids, the magnetic particles may be configured to bind to the nucleic acids by other physical interactions (e.g., charge/crowding interactions).

In various embodiments, the isolation material may include antibodies that selectively bind to receptors on a particular cell's surface. In various embodiments, the magnetic particles may also bind to (or be captured by) the antibodies that selectively bind to receptors on the cell surface. In various embodiments, the antibodies may be configured to bind to receptors on a target cell or a non-target cell surface.

In various embodiments, the isolation material includes a polymer (e.g., polyamide, PTFE, polychloroprene, polyimide, polyacrylonitrile) wool configured to sequester a target cell and allow non-target cells to be removed (e.g., washed out) from the cell suspension. In various embodiments, one or more magnets may be placed within the inner chamber 103 to secure the polymer wool and prevent relative motion of the polymer wool as the assembly is rotated. In various embodiments, rotation of the torus assembly having a polymer wool in the inner chamber minimizes the tendency of target cells to irreversibly bind to the polymer wool.

In various embodiments, the amount of polymer wool disposed within the inner chamber may be determined based on the below table. In various embodiments, the polymer wool may include any suitable shape, such as, for example, randomly distributed fibers, honeycomb, and/or a woven material. In various embodiments, the polymer wool may operate as a depth filter if the density of fibers is high. In various embodiments, the polymer wool density and mass may be adjusted as suitable for the particular use.

Figure 1B:
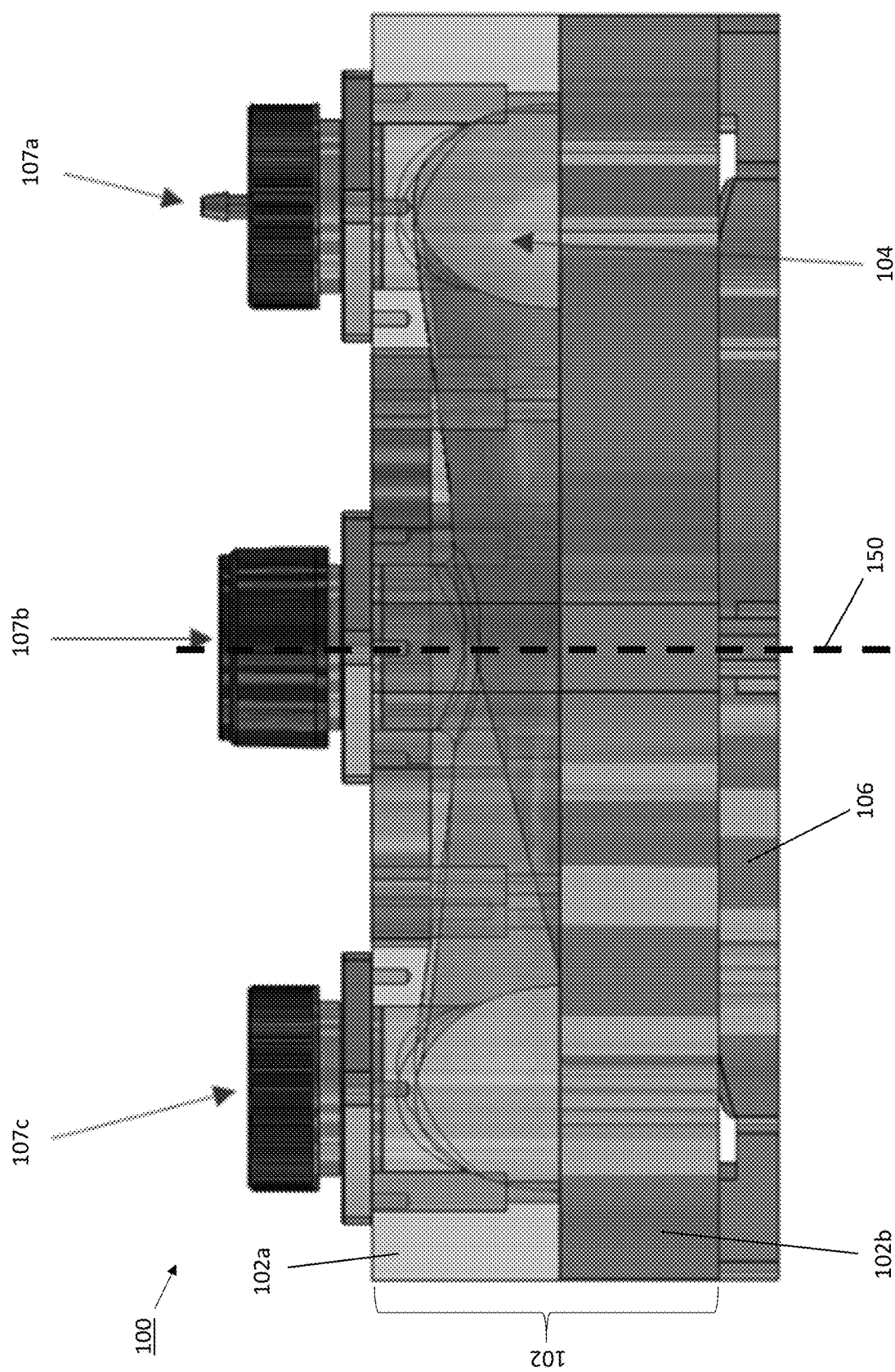
FIG. 1B illustrates a side view of an exemplary cell isolation and culture assembly according to embodiments of the present disclosure.

FIG. 1B illustrates a side view of an exemplary assembly 100 according to embodiments of the present disclosure. As shown in FIG. 1B, the semi-toroidal shape of the inner chamber defines a longitudinal axis 150.

In various embodiments, the torus assembly may be used to process and expand adherent cells. In various embodiments, the material compromising the inner surface of the torus can be modified or selected to encourage the binding of adherent cells to the surface of the torus. In various embodiments, alternatively (or additionally), the apparent surface area can be increased by operating the torus with microparticles added to the culture that will allow the adherence of a number of cells to a single particle, thus maintaining an adherent culture condition for the cells while also leveraging the movement of the cellular material around the torus as it rotates.

Figure 2:
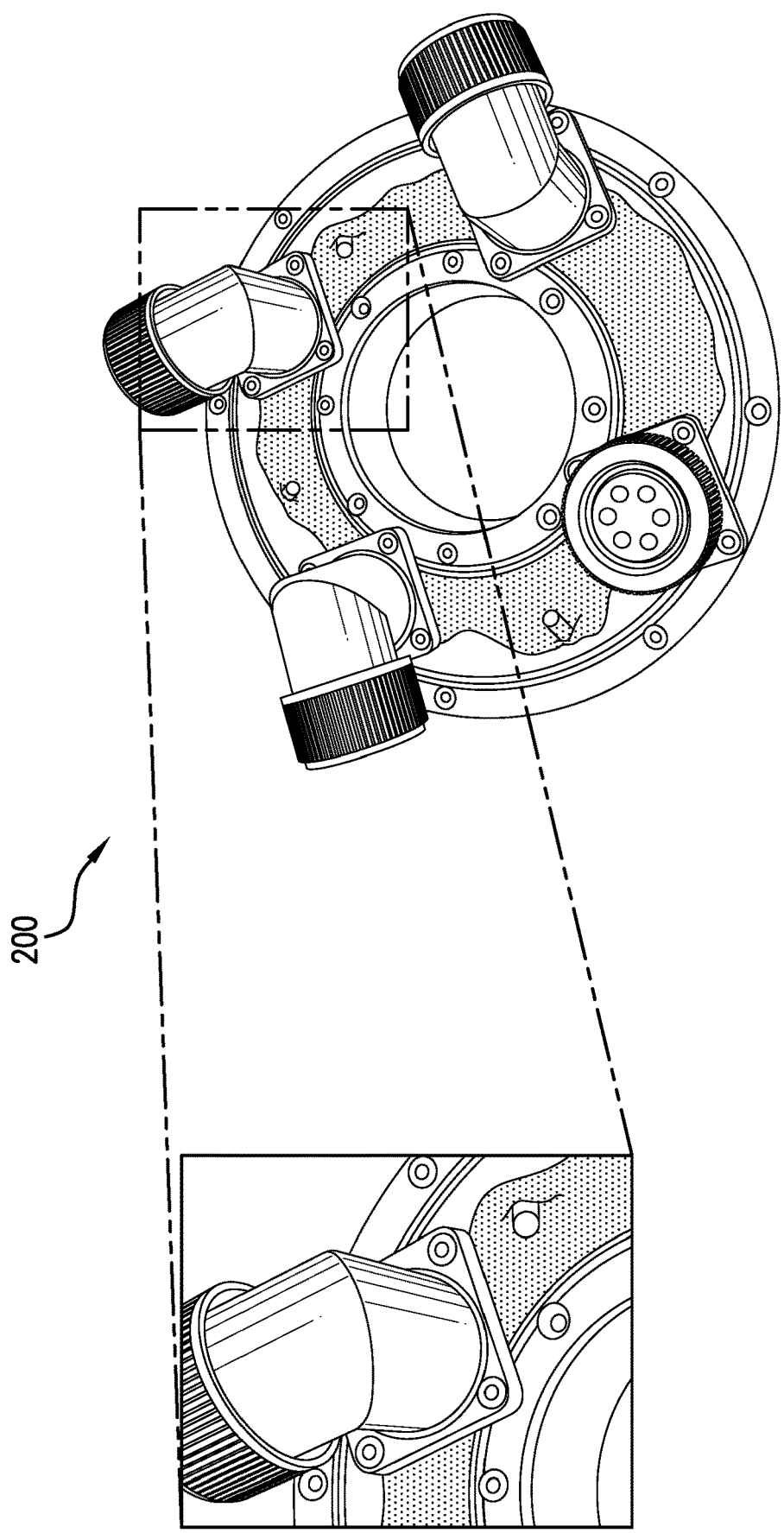
FIG. 2 illustrates an exemplary cell isolation and culture assembly according to embodiments of the present disclosure.

FIG. 2 illustrates an exemplary cell isolation and culture assembly 200 according to embodiments of the present disclosure. The assembly 200 shown in FIG. 2 includes three gas exchange vents (e.g., filter caps) and a single sample access port for introduction of a sample (e.g., a cell suspension).

A process flow for cell isolation according to embodiments of the present disclosure may include introducing a sample (e.g., a cell suspension) into the inner chamber of the torus assembly having a polymer wool disposed therein. In various embodiments, the polymer wool only covers a portion of the inner chamber. The cell suspension may include T-cells, natural killer cells, B-cells, PBMCs, apheresis materials, whole blood, and/or monocytes. The cell suspension may be incubated at e.g., 5% CO2 at 37 degrees Celsius for a predetermined amount of time as the torus assembly is rotated. In various embodiments, isolation may occur under standard atmosphere and temperature (e.g., 1 atm and 20-22 degrees Celsius). In general, the target cells (e.g., T-cells) will release along with the natural killer cells while the B-cells and monocytes remain on the polymer wool. In various embodiments, the polymer wool may be removed and disposed of. Thus, the remaining target cells may be isolated.

In various embodiments, the quantity of cells may be 5-30 million cells. In various embodiments, a polymer wool mass range may be between about 0.025 g to about 0.15 g. In various embodiments, the quantity of cells may be about 50 million to about 1 billion cells. In various embodiments, the polymer wool mass range may be about 0.25 g to about 2.5 g. In various embodiments, at least 0.2 g of polymer wool may be used. In various embodiments, the density of the polymer wool may be at least 0.1 g/cc. For example, at a density of 0.1 g/cc, a mass of polymer wool of 0.2 g to 2.5 g would occupy about 2 cc to about 25 cc of volume.

In various embodiments, the assembly may include a nested torus arrangement. For example, a first torus assembly may be nested within an inner chamber of a second torus assembly. In various embodiments, the first torus assembly may include a trap door that, when opened, allows the cells not captured by the isolation material (e.g., polymer wool) to be released without risking contamination of the cells that would otherwise occur if the inner chamber was exposed to air for any reason (e.g., to dispose of the polymer wool after use). In some embodiments, the trap door can be hingedly coupled to the torus wall(s); in some embodiments the trap door can be translated, e.g. in a telescoping manner, parallel to an adjacent torus wall.

In various embodiments, the torus reactor assembly may be rotated at a speed of 0 mHz to about 200 mHz. In various embodiments, the torus reactor assembly may be rotated at a speed of about 83 mHz. In various embodiments, the torus reactor assembly may be rotated at a speed of less than 90 mHz. In various embodiments, the torus reactor may be rotated at a speed higher than 200 mHz.

FIGS. 3A-3D illustrate a modular installation 310 (e.g., a frit) disposed within the inner chamber of the assembly according to embodiments of the present disclosure. In various embodiments, as shown in FIGS. 3A-3D, one or more modular installations 310 may be placed within the inner chamber such that the installation is in the path of the cell suspension. In various embodiments, modular installations 310 may be used for control or restriction of the cell suspension flow. In various embodiments, modular installations 310 may include a packed frit for cell-chromatography-like isolation. In various embodiments, the modular installation 310 may include one or more arms 311 extending therefrom. In various embodiments, the arms 311 may extend from a single origin point. In various embodiments, the arms 311 may extend at differing angles from the origin point. In various embodiments, the modular installation 310 may include one or more slits 312 (e.g., horizontal and/or vertical slits). In various embodiments, the one or more slits 312 may be configured to direct/alter flow of the cell suspension as the assembly is rotated. In various embodiments, the angles of incidence of the arm(s) 311 and/or slit(s) 312 can be adjusted to allow the maximum passage of cellular material into and out of the frit with minimal surface area exposed to the incoming material. In various embodiments, the modular installations may include a wide-bore mesh of open holes. In various embodiments, secured polymer wool (e.g., via magnets, frits, and/or barriers) may lead to a more rapid distribution of liquid as loose polymer wool may allow material to slip along the housing wall without passing through the polymer wool.

Figure 3B:
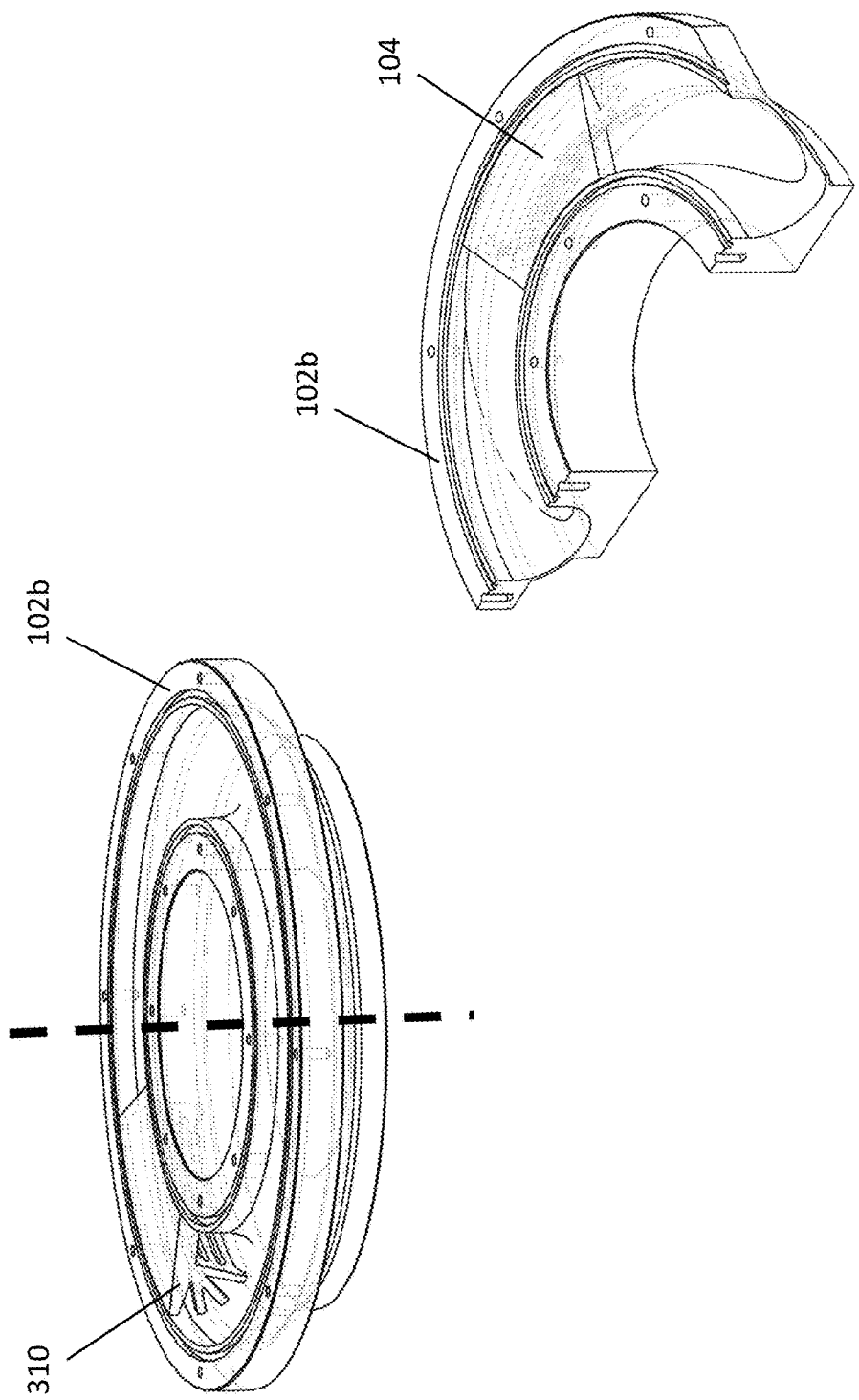
Figure 3C:
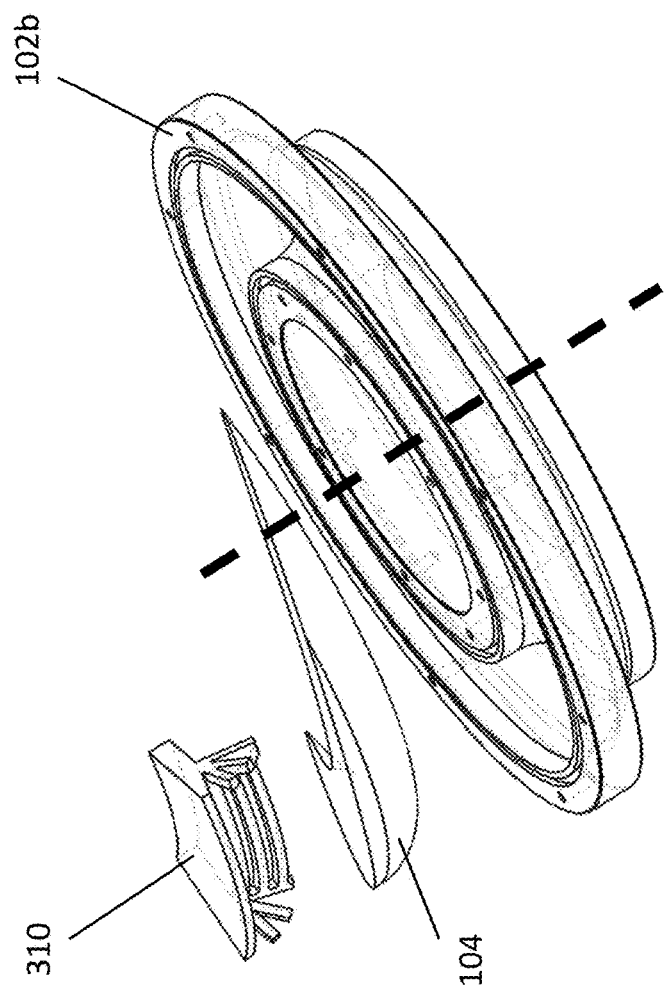
Figure 3D:
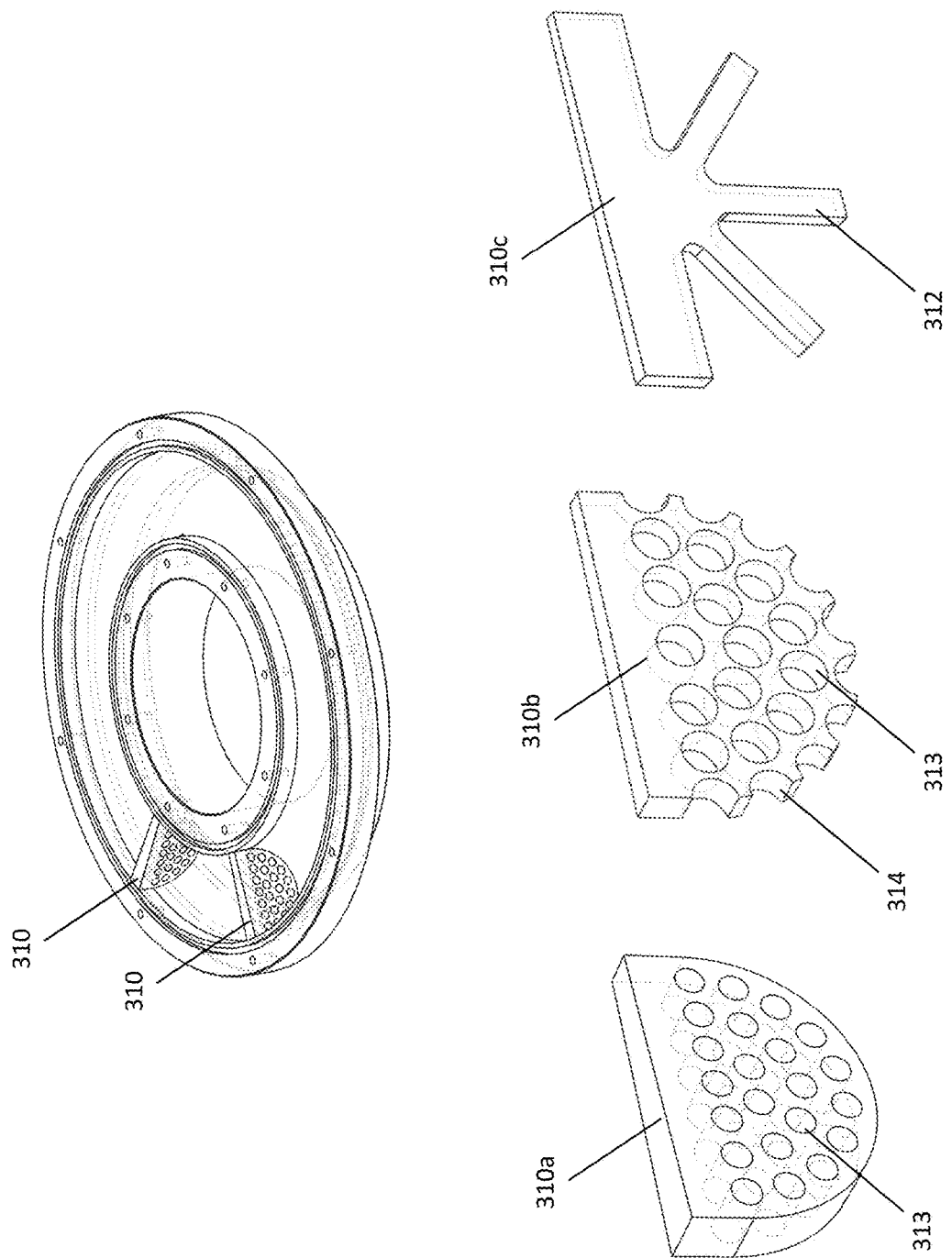

FIG. 3D further illustrates various other embodiments of a modular installation 310. For example, a modular installation 310a may include one or more holes 613. In various embodiments, as shown by modular installations 310a and 310b, the modular installation may not include any arms. In another example, a modular installation 310b may include one or more holes 313 in addition to cuts 314 (e.g., semicircular) along the outermost edge of the modular installation 301b. In various embodiments, the holes 313 may be any suitable size and may include any suitable arrangement such as a uniformly distributed arrangement or non-uniform arrangement, (e.g., a gradient) to either allow the passage of material and/or restrict the passage of material. For example, the holes may allow the passage of cells, but restrict the flow of larger objects in suspension. In various embodiments, a modular installation 310c may include any suitable number of arms 312 extending therefrom. For example, modular installation 310c includes three arms 312 radiating outward from a central point. In various embodiments, the modular installation 310 comprises a mesh material.

In various embodiments, the purity of the target material after an isolation process in the torus reactor assembly may be greater than 50%. In various embodiments, the purity of the target material after an isolation process in the torus reactor assembly may be greater than 60%. In various embodiments, the purity of the target material after an isolation process in the torus reactor assembly may be greater than 70%. In various embodiments, the purity of the target material after an isolation process in the torus reactor assembly may be greater than 80%. In various embodiments, the purity of the target material after an isolation process in the torus reactor assembly may be greater than 90%. In various embodiments, the yield of the target material after an isolation process in the torus reactor assembly may be greater than 20%. In various embodiments, the yield of the target material after an isolation process in the torus reactor assembly may be greater than 30%. In various embodiments, the yield of the target material after an isolation process in the torus reactor assembly may be greater than 40%. In various embodiments, the yield of the target material after an isolation process in the torus reactor assembly may be greater than 50%. In various embodiments, the yield of the target material after an isolation process in the torus reactor assembly may be greater than 60%. In various embodiments, the yield of the target material after an isolation process in the torus reactor assembly may be greater than 70%. In various embodiments, the yield of the target material after an isolation process in the torus reactor assembly may be greater than 80%. In various embodiments, the yield of the target material after an isolation process in the torus reactor assembly may be greater than 90%. One of skill in the art will recognize that purity and/or yield may be optimized for each type of target material experimentally, for example, by adjusting the speed of rotation of the torus reactor assembly. Moreover, one skilled in the art will recognize that optimizing for one variable (e.g., either purity or yield) may not optimize the other variable (e.g., either purity or yield).

Figure 4A:
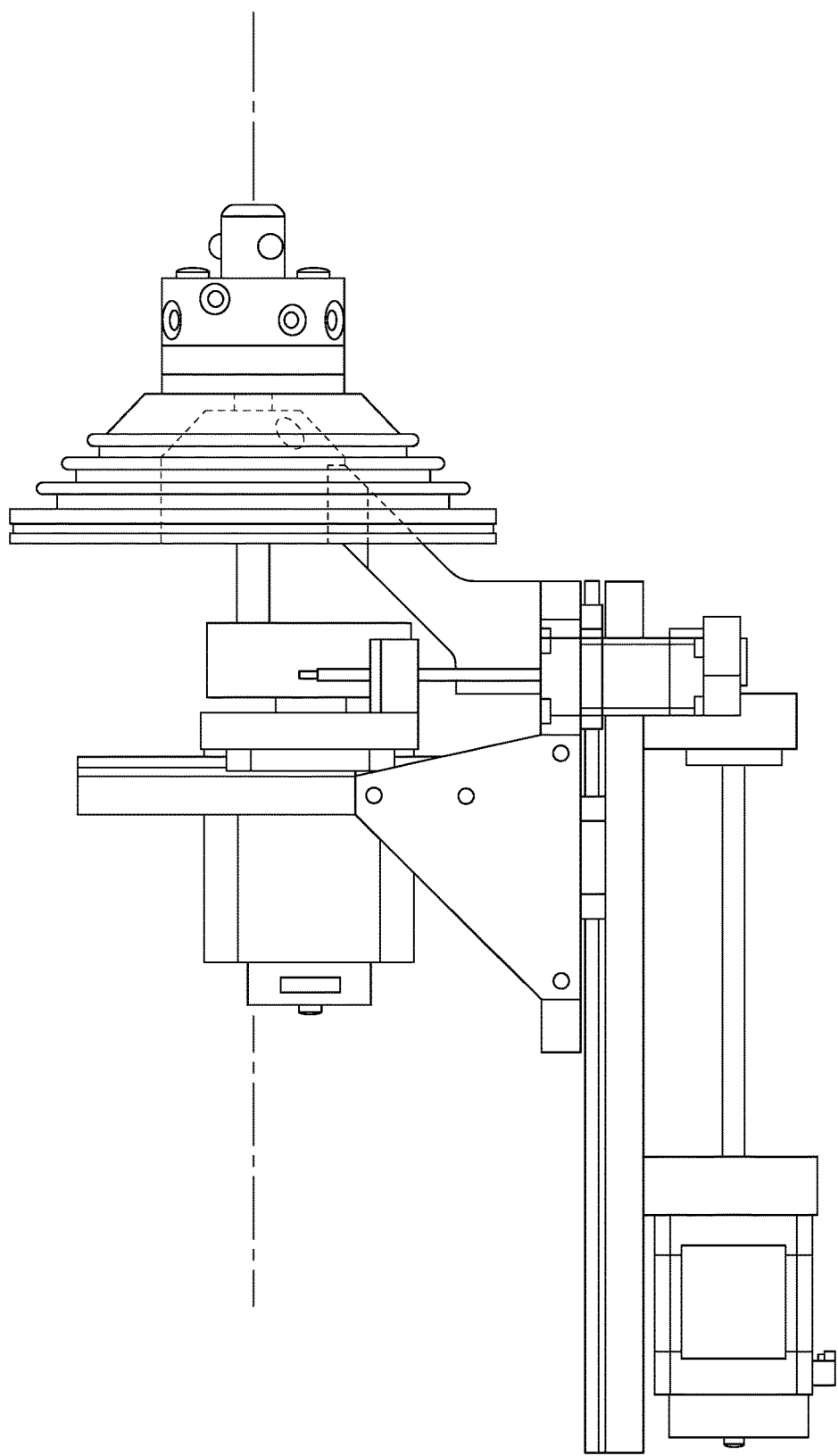
FIGS. 4A-4D illustrate a swash actuator mechanism according to embodiments of the present disclosure.
Figure 4B:
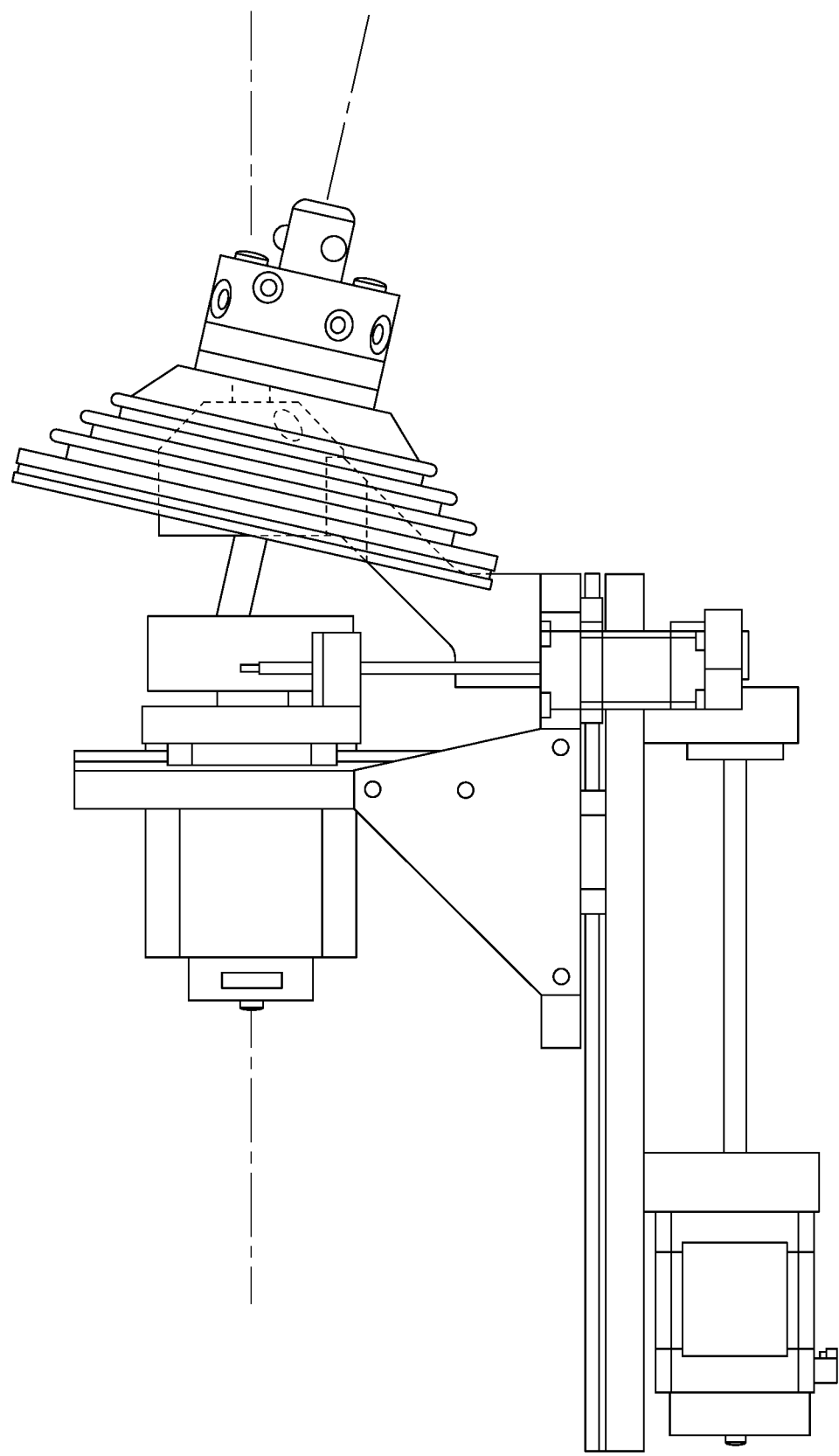
Figure 4D:
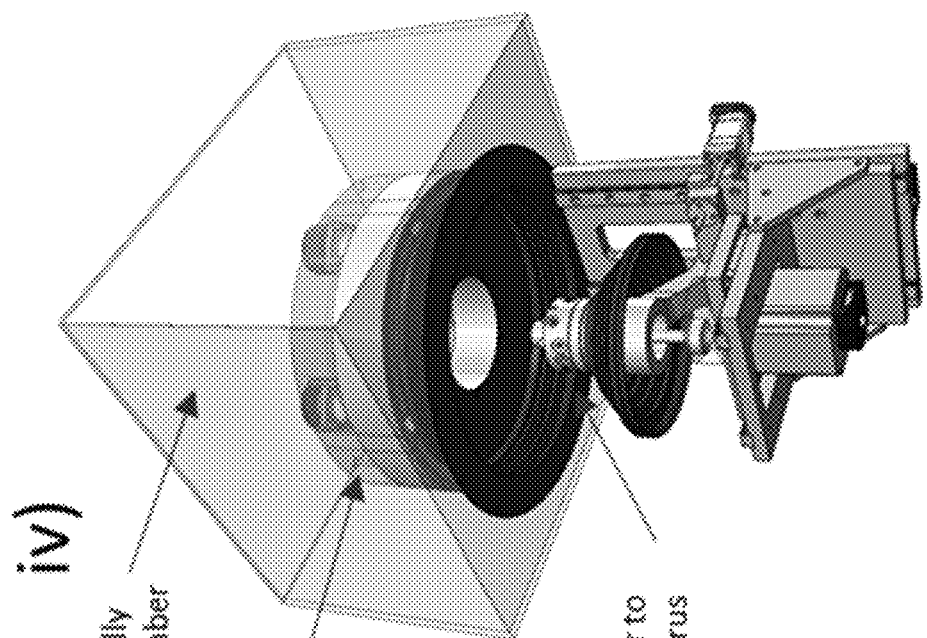
Figure 4C:
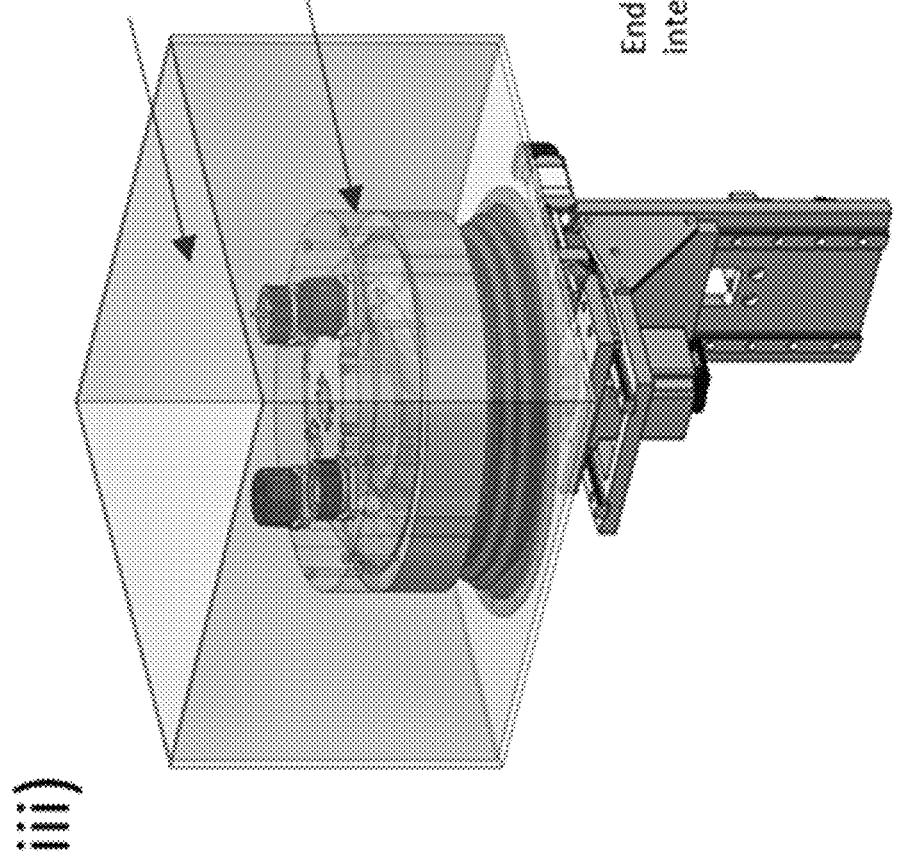

FIGS. 4A-4D illustrate a swash actuator mechanism according to embodiments of the present disclosure. As shown in FIG. 4A, the swash actuator mechanism is configured to interface with the torus assembly shown in FIGS. 1A-1B. As shown in FIG. 4B, the axis of rotation of the swash actuator mechanism may be adjusted via an articulation joint that allows the angled rotation of the torus assembly (not shown) to enable mixing and swirling of the contents within the inner chamber of the torus assembly. As shown in FIG. 4C, a torus assembly interfaces with the swash actuator mechanism and is housed in an environmentally controlled chamber for cell culture. In various embodiments, the environmentally controlled chamber may control temperature, humidity, and/or gases (e.g., $CO_2$, $O_2$) within the chamber. In particular, the end effector of the swash actuator mechanism is engaging the central hole of the torus assembly such that rotation of the end-effector causes rotation of the torus assembly within the environmentally controlled chamber (i.e., the swash actuator mechanism is in the engaged position. As shown in FIG. 4D, the end-effector is disengaged from the central hole of the torus assembly (i.e., the swash actuator mechanism is in the disengaged position). In various embodiments, the swash actuator mechanism may be installed within a standard culture incubator as is known in the art or a self-contained incubator.

In various embodiments, the torus assembly may be rotated by the swash actuator mechanism at a constant speed. In various embodiments, the torus assembly may be rotated by the swash actuator mechanism at alternating/varying speeds. In various embodiments, the torus assembly may be intermittently rotated by the swash actuator mechanism (e.g., start and stop).

In various embodiments, the torus assembly may be rotated at a speed of no more than 200 mHz. In various embodiments, the torus assembly may be rotated at a speed greater than 200 mHz. In various embodiments, the torus assembly may be rotated at a speed of no more than 83 mHz. In various embodiments, the torus assembly may be rotated at a speed greater than 83 mHz. In various embodiments, the torus assembly may be rotated at a speed of up to 8.3 mHz. In various embodiments, highest purity may be achieved when incubation is static (i.e., no rotation). In various embodiments, some rotation/movement may increase yield. In various embodiments, the torus assembly may be rotated at a speed of lower than 8.3 mHz. In various embodiments, the torus assembly may be rotated at a speed of 0.83 mHz.

In various embodiments, rotation may be performed up to 3 hours. In various embodiments, rotation may be performed for up to 2 hours (e.g., when rotated at 8.3 mHz). In various embodiments, rotation may be performed for days or weeks.

Figure 5A:
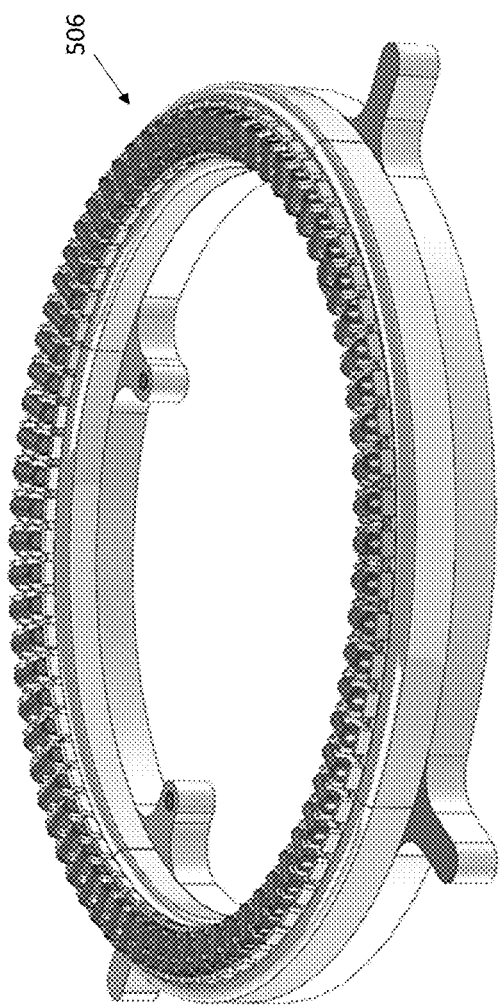
FIG. 5A illustrates a magnetic ring according to embodiments of the present disclosure.
Figure 5C:
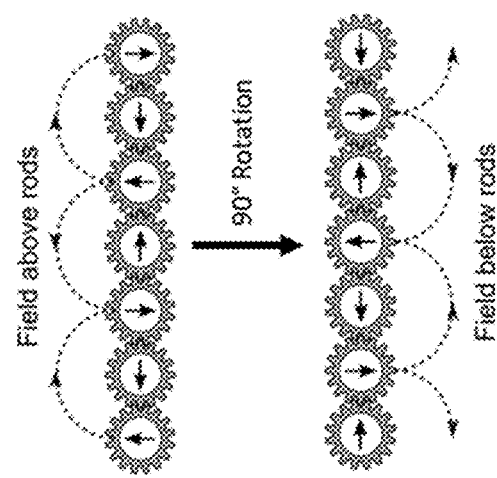
FIGS. 5B-5C illustrate various magnetic fields according to embodiments of the present disclosure.
Figure 5B:
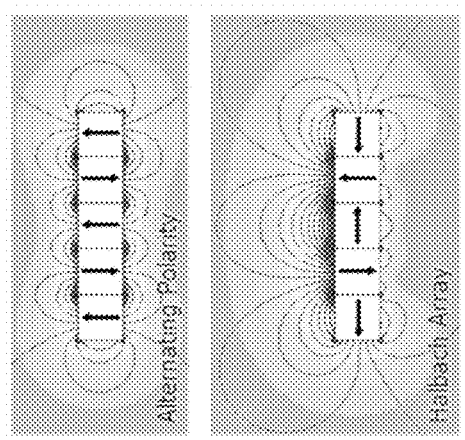

FIG. 5A illustrates a magnetic ring according to embodiments of the present disclosure. FIGS. 5B-5C illustrate various magnetic fields according to embodiments of the present disclosure. In particular, FIG. 5A illustrates an example of a magnetic ring 506 that may interface with the torus assembly when a local magnetic field is required for cell isolation. The magnetic ring 506 is shown with a plurality of magnets arranged around the circumference of the upper surface of the ring 506. In various embodiments, the magnetic ring 506 may be assembled such that there are gaps in the magnetic field to allow for fluidic interaction or other interactions where local absence of a magnetic field (or reduced strength magnetic field) is advantageous. Referring back to FIGS. 1A-1B, the magnetic ring 106, 506 may be coupled to the bottom surface of the lower portion of the housing 102b. FIG. 5B illustrates various orientations in which permanent magnets may be arranged to take advantage of the physics of magnetic fields. For example, orientations are shown here for a standard Alternating Polarity field (advantageous for assembly as it may minimize the tendency of magnets to be pushed out of the grips due to non-ideal pole-to-pole alignment). In another example, permanent magnets may be arranged in a Halbach Array orientation where the magnetic field is concentrated on one side of the array and weak on the other. FIG. 5C illustrates the local magnetic field (as experienced by material within the torus) generated by a Halbach array that can be switched on/off by rotating the magnets 180° around the long axis to switch the direction of the field towards/away from the torus.

In various embodiments, the strength of the magnetic field may be gradually adjusted by, for example, controlled movement of the magnetic ring 506. In one example, moving the magnetic ring 506 closer to the sample (inside the torus reactor assembly) increases magnetic field, while moving the magnetic ring 506 away from the sample reduces the magnetic field. In various embodiments, the magnetic field may be gradually increased (e.g., by a constant or variable rate) during the isolation process (e.g., throughout the entire isolation process). In various embodiments, the magnetic field may be gradually decreased (e.g., by a constant or variable rate) during the isolation process (e.g., throughout the entire isolation process). In various embodiments, the magnetic field may be alternated between increasing and decreasing during the isolation process. For example, the magnetic field may be increased then decreased (or decreased then increased) during one cycle of the isolation process. The magnetic field may be cycled any suitable number of times (e.g., 1 time, 2 times, 3 times, 4 times, 5 times, 6 times, 7 times, 8 times, 9 times, 10 times, etc.) to provide adequate isolation of one or more target materials. In various embodiments, adequate isolation may be determined based on a desired purity and/or desired yield of target material.

FIG. 6 illustrates steps in a process for cell isolation according to embodiments of the present disclosure. In particular, FIG. 6 shows image frames captured from a cell-magnetic experiment performed on a torus device with an 80% alternating polarity magnetic array that was switched on and off by physical proximity. On the left, the torus is shown when the cells/beads are present without any magnetic field. The middle image shows the clarification of the magnetic material to the magnetic loci when the field is present (approx. 30 sec), and on the right is the resuspension of the isolated material following subsequent removal of the field (approx. 40 sec). Rotation of the torus (e.g., 3D rotation) assembly via the end effector and motor is ongoing throughout all steps in the process.

Figure 7A:
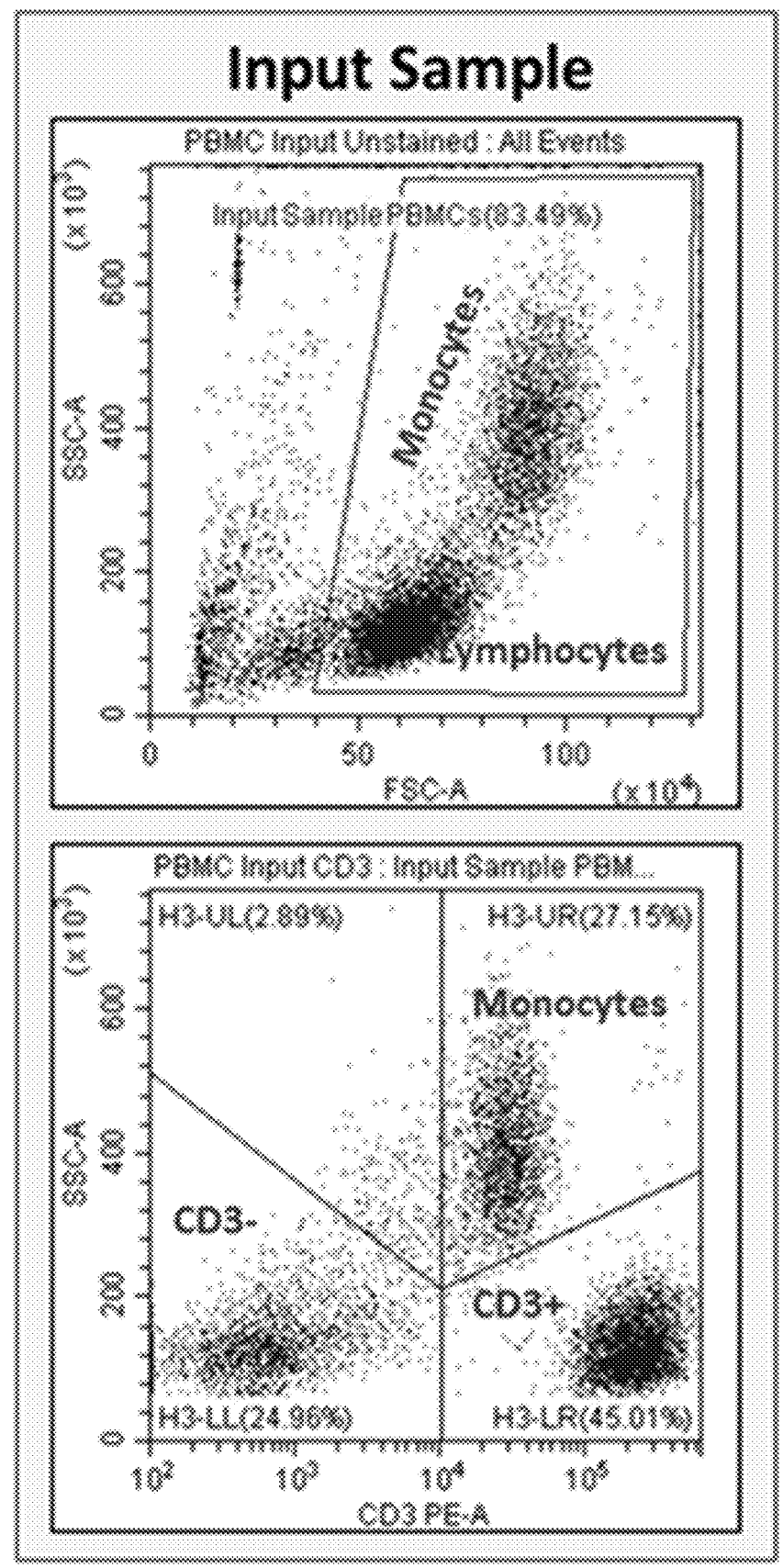
FIGS. 7A-7C illustrate 2D plots demonstrating results of cell isolation between a manual protocol and a torus protocol according to embodiments of the present disclosure.
Figures 7B, 7C:
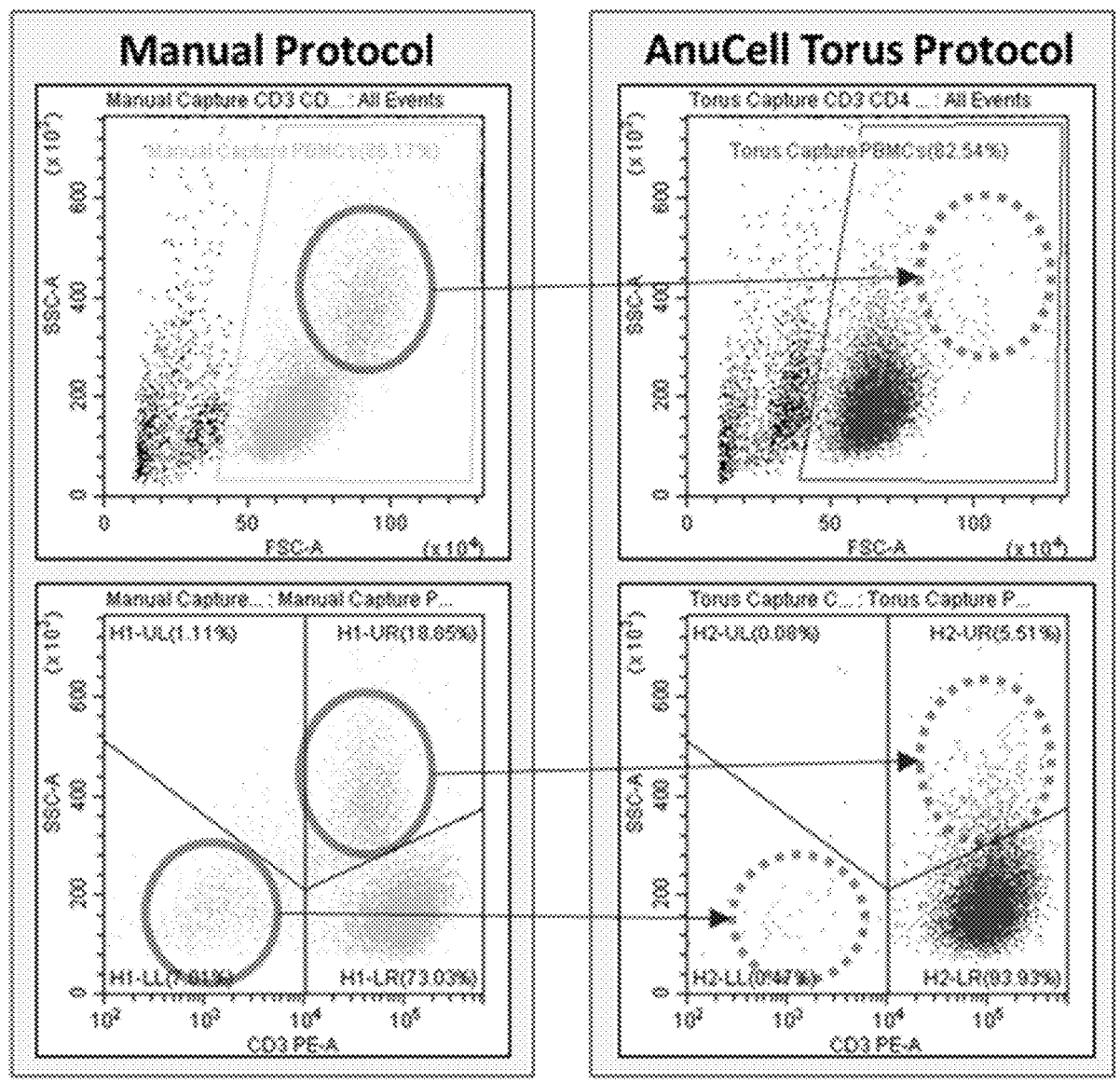

FIGS. 7A-7C illustrates 2D plots demonstrating results of cell isolation between a manual protocol and a torus protocol according to embodiments of the present disclosure. In particular, FIGS. 7A-7C illustrate data from an experiment where equal numbers of input PBMCs (FIG. 7A) were isolated using the magnetic protocol from a prior art protocol by either the recommended manual method (FIG. 7B), or using a torus assembly described herein (FIG. 7C). Following analysis by flow cytometry, the purity of CD3+ cells using the torus assembly was higher, as shown by fewer monocytes and CD3− cells.

In various embodiments, an isolation process performed within a torus reactor assembly as described herein may result in a higher percentage of target material (e.g., T-cells) in a suspension than what was originally loaded into the torus reactor assembly (e.g., PBMCs originally loaded into the torus reactor). In one example, the percentage of T-cells in a PBMC suspension loaded into a torus reactor assembly may be between 50% and 60% (with other non-target material, such as, for example, monocytes, B-cells, NK cells and/or other remnants in the suspension). In various embodiments, after an isolation process is performed for a predetermined period of time (e.g., about 10 min to about 180 min), the percentage of T-cells in the PBMC suspension may increase to higher than 60%. In various embodiments, the percentage of T-cells in the PBMC suspension may increase to higher than 70%. In various embodiments, the percentage of T-cells in the PBMC suspension may increase to higher than 80%. In various embodiments, the percentage of T-cells in the PBMC suspension may increase to higher than 90%.

Figure 8A:
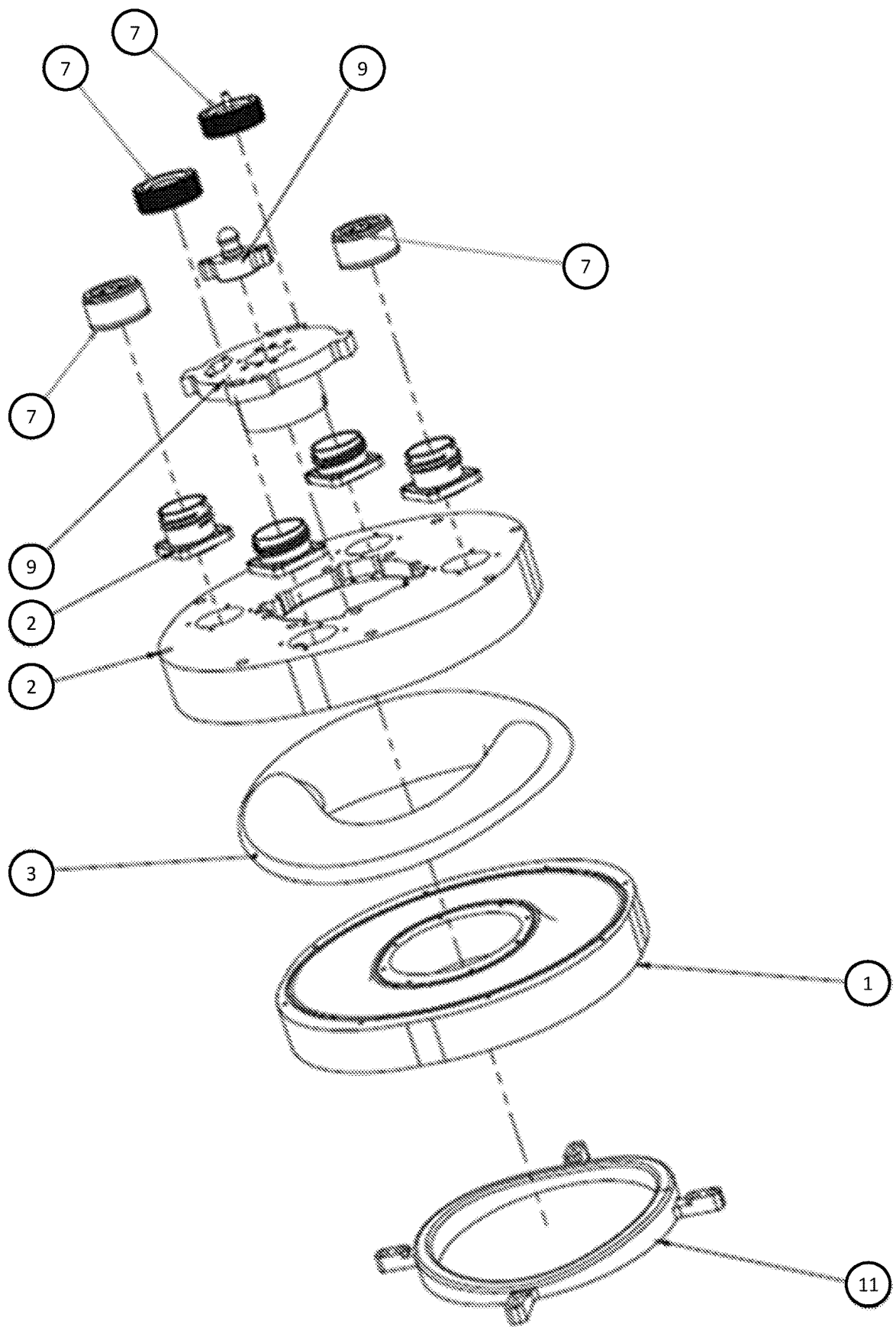
FIGS. 8A-8B illustrate a mechanical drawing of a twisted torus assembly according to embodiments of the present disclosure.
Figure 8B:
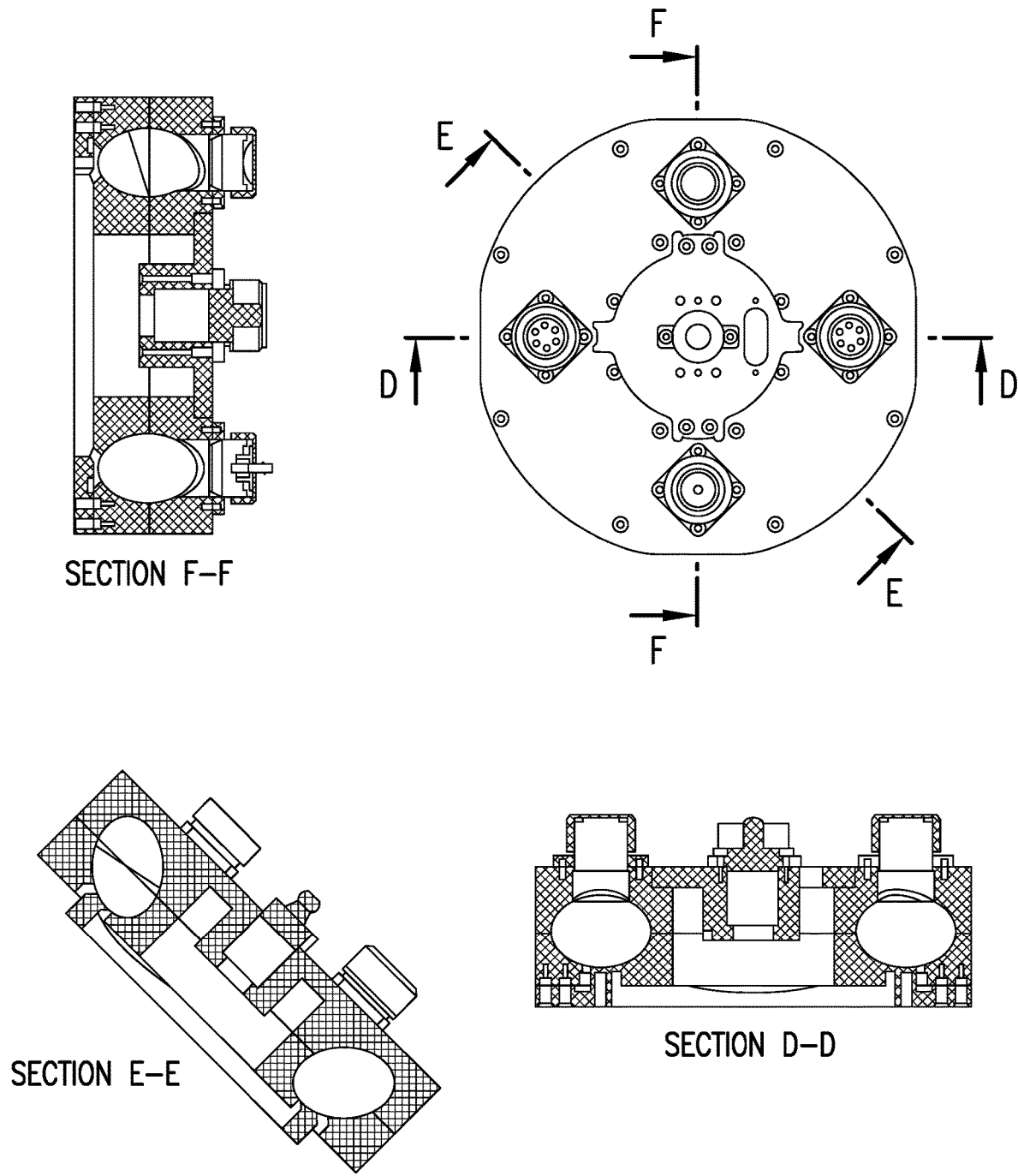

FIGS. 8A-8B illustrate a mechanical drawing of a twisted torus assembly according to embodiments of the present disclosure. In such configurations the fluid channel can be formed with fixed internal dimensions, but twisted so that the entire torus does not lie in a single plane. As shown in cross-sectional view F-F of FIG. 8B, the internal fluid channel (shown as a generally elliptical cross-section in this exemplary embodiment) has a first orientation with respect to the horizontal, and a second "tilted" or offset angle in cross sectional cross-sectional view E-E.

Figure 9:
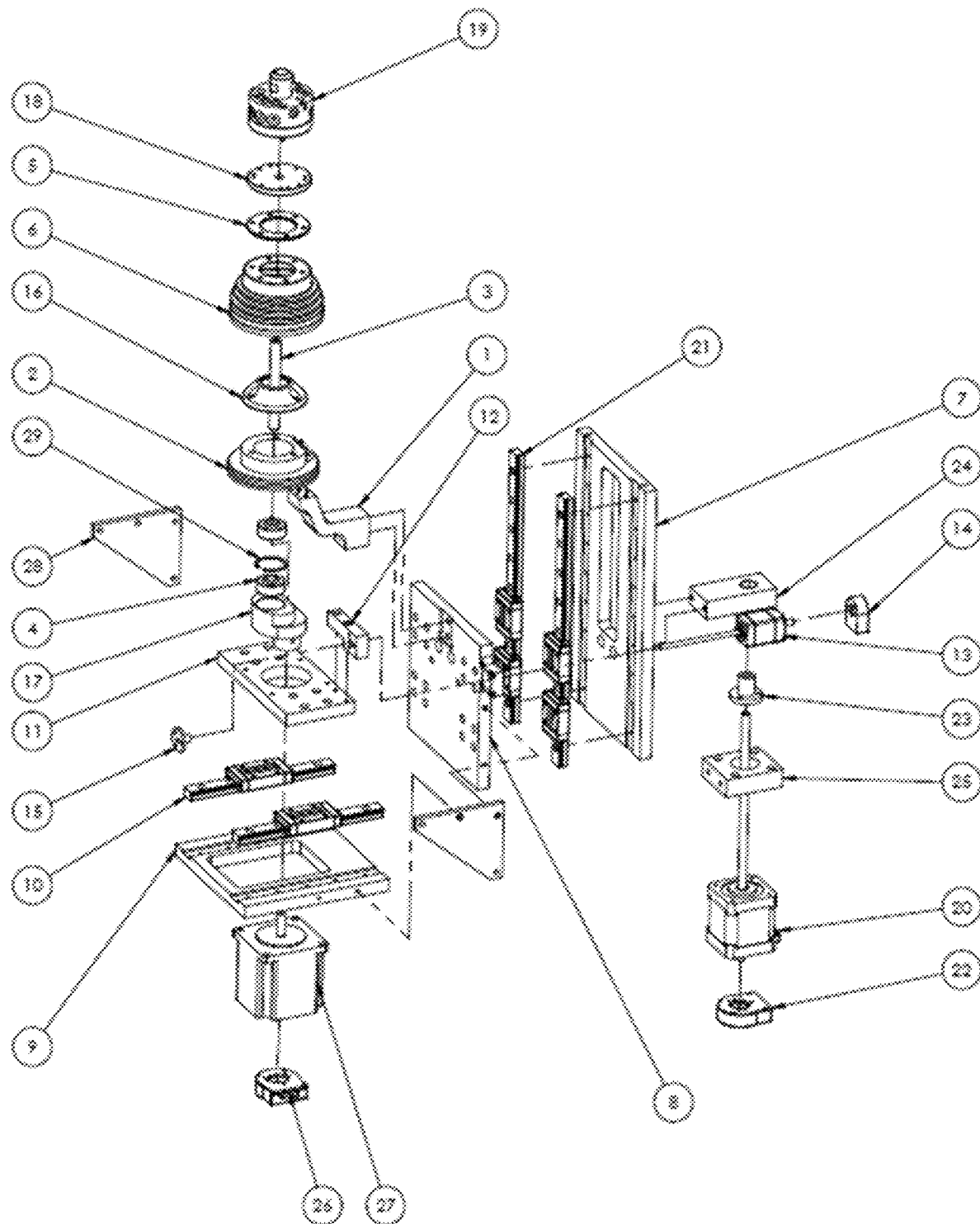
FIG. 9 illustrates a mechanical drawing of swash actuator mechanism according to embodiments of the present disclosure.

FIG. 9 illustrates a mechanical drawing of swash actuator mechanism (exploded view) according to embodiments of the present disclosure.

FIG. 10 illustrates a method 1000 of isolating target cells and culturing the target cells according to embodiments of the present disclosure. At 1002, an assembly is provided. The assembly includes a housing having an upper portion and a lower potion defining an inner chamber. The inner chamber includes a semi-toroidal shape. The semi-toroidal shape defines a longitudinal axis. The assembly further includes one or more fluidic connections to the inner chamber. The assembly further includes an isolation material disposed within the inner chamber that is selected from the group consisting of a polymer wool and magnetic particles. The assembly further includes a magnetic ring releasably coupled to the housing and the magnetic ring comprising one or more permanent magnets. At 1004, a suspension is loaded into a fluidic connection. The suspension includes the target material and the one or more non-target materials. At 1006, the assembly is engaged with a platform. The platform is operably coupled to a motor. At 1008, the motor is activated to rotate the assembly about the longitudinal axis thereby causing either the target material or one or more non-target materials to interact with the isolation material. At 1010, either the target material or the one or more non-target materials are extracted from the assembly that did not interact with the isolation material thereby isolating the target material or the non-target material within the assembly.

Figure 11A:
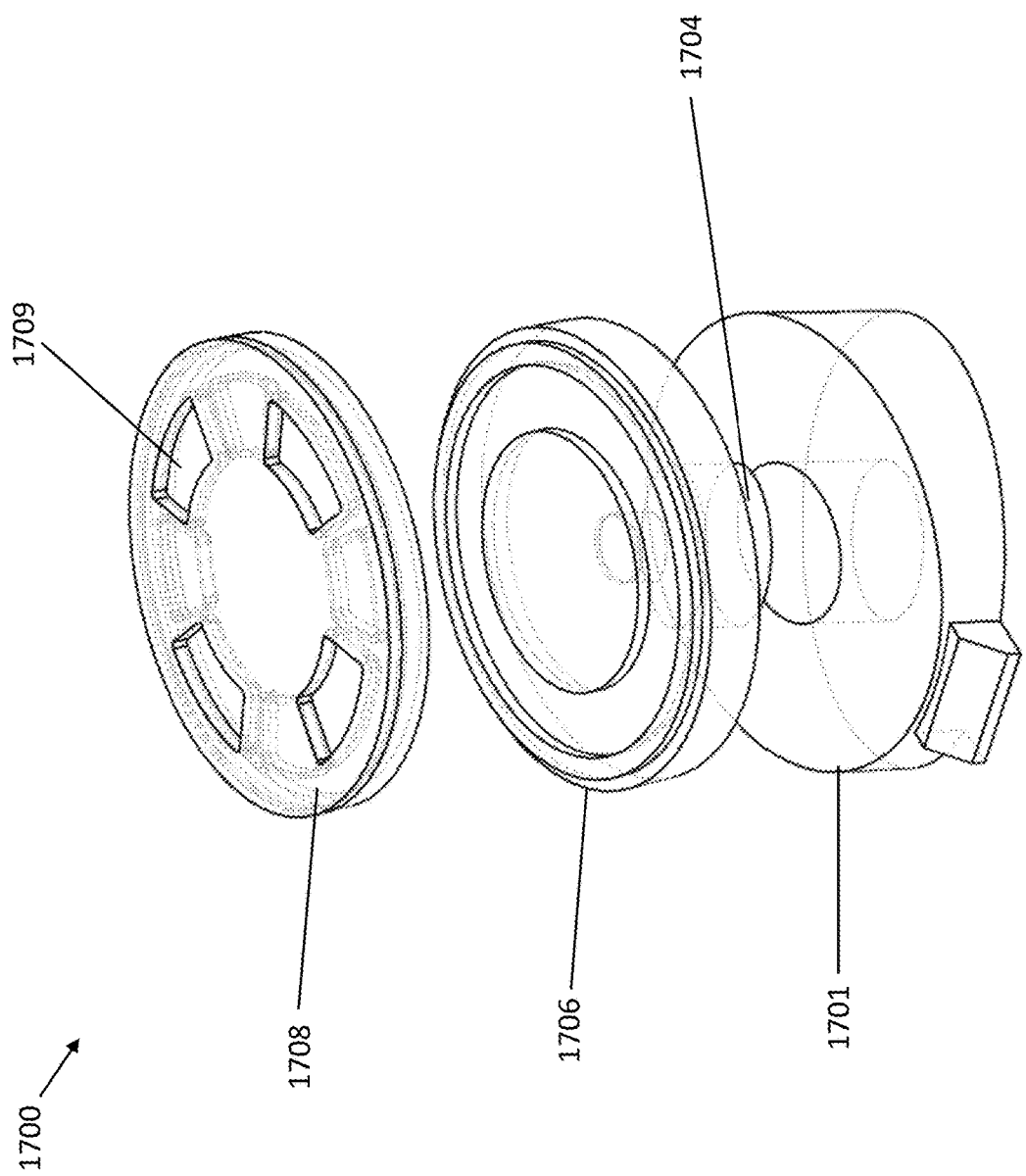
FIG. 11A illustrates a system for rotating a target material isolation assembly according to embodiments of the present disclosure.
Figure 11B:
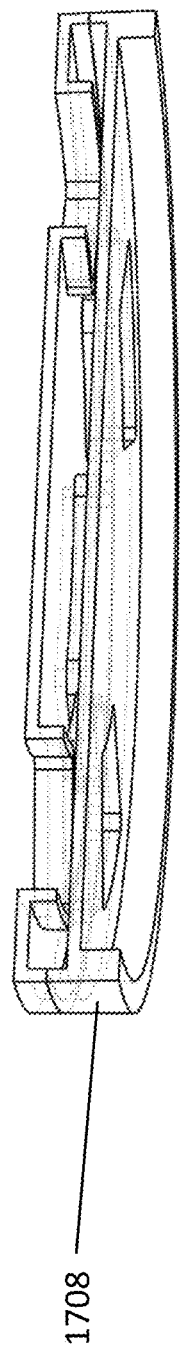
FIG. 11B illustrates a cross section of a lid of the system according to embodiments of the present disclosure.
Figure 11C:
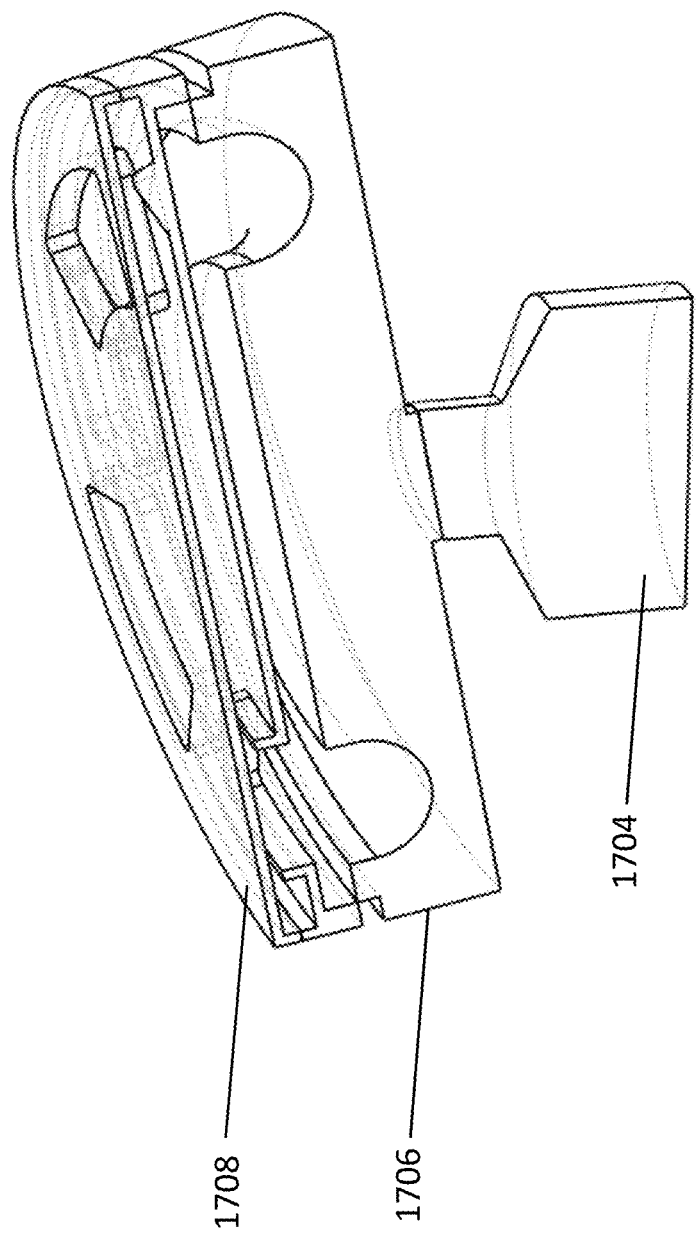
FIG. 11C illustrates a cross section of the system (without a dock) according to embodiments of the present disclosure.

FIG. 11A illustrates a system 1100 for rotating a target material isolation assembly according to embodiments of the present disclosure. In particular, FIG. 11A shows a dock 1101 (e.g., an intelligent dock) that operably couples with a motor 1104 and an assembly holder 1106 into which an assembly of the present disclosure would be contained. The system 1100 further includes a lid 1108 that is releasably affixed to the top of the holder 1106. In various embodiments, the lid 1108 includes one or more openings 1109. In various embodiments, the one or more openings 1109 may correspond to the openings/ports of an assembly to thereby provide access to the openings/ports while confining the assembly within the holder. In various embodiments, the lid 1108 may include an upper portion having one or more openings that is rotatably attached to a lower portion having one or more openings. When the upper portion is rotated such that the openings in the upper portion align with the openings in the lower portion, access is provided to the interior of the holder 1106. FIG. 11B illustrates a cross section of a lid of the system according to embodiments of the present disclosure. FIG. 11C illustrates a cross section of the system (without a dock) according to embodiments of the present disclosure.

Figure 12A:
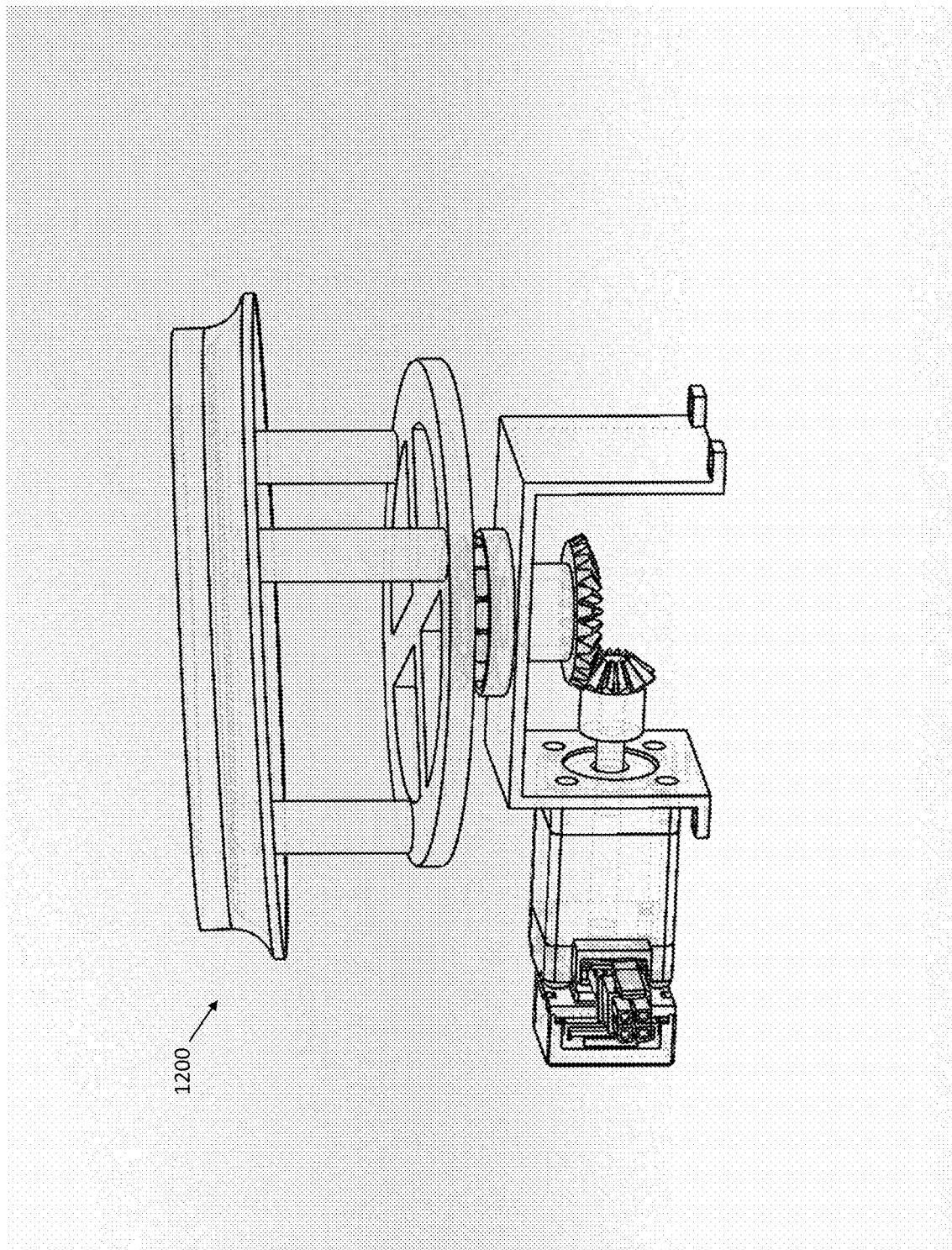
FIGS. 12A-12C illustrate a motor assembly according to embodiments of the present disclosure.
Figure 12B:
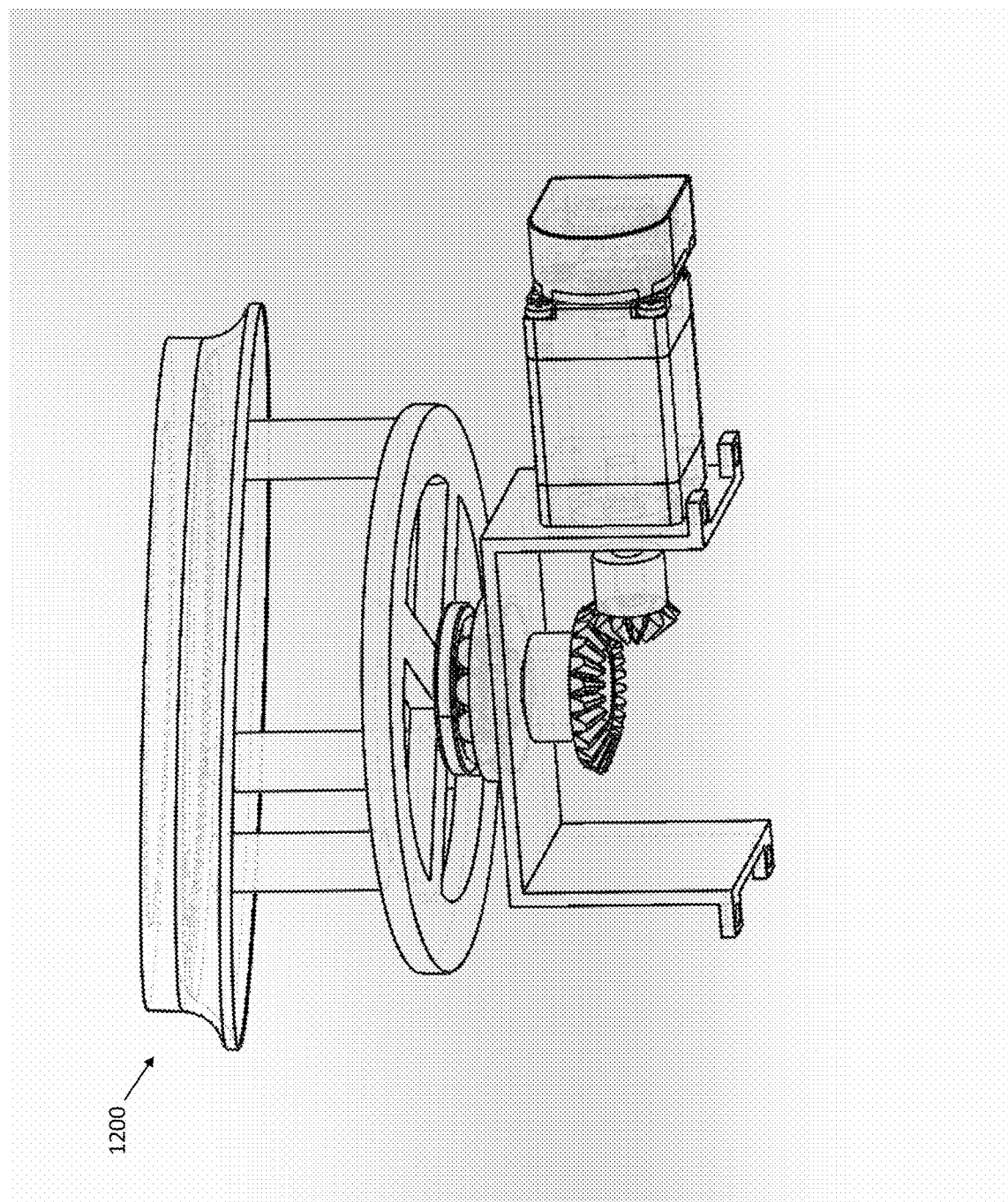
Figure 12C:
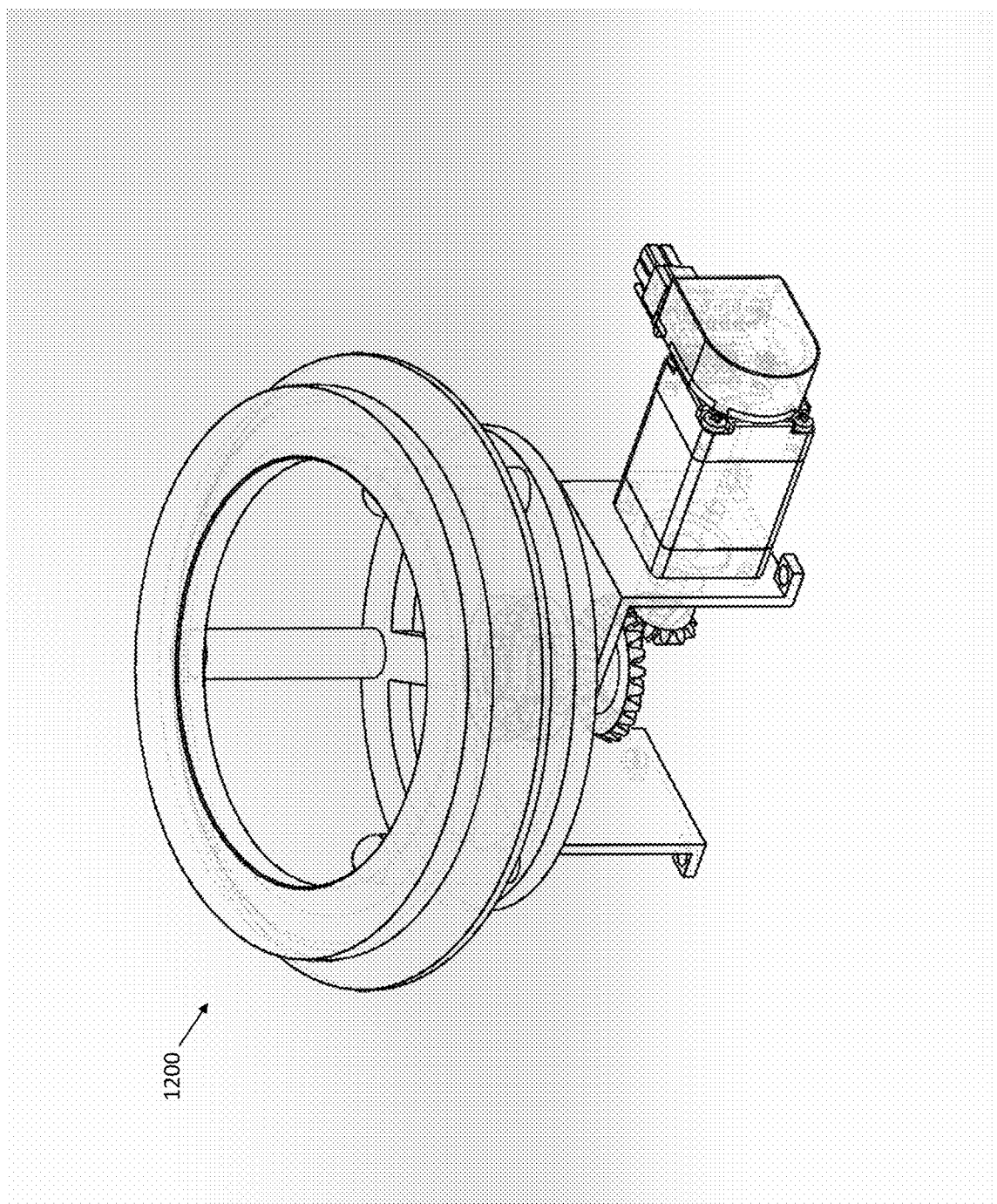
Figure 13A:
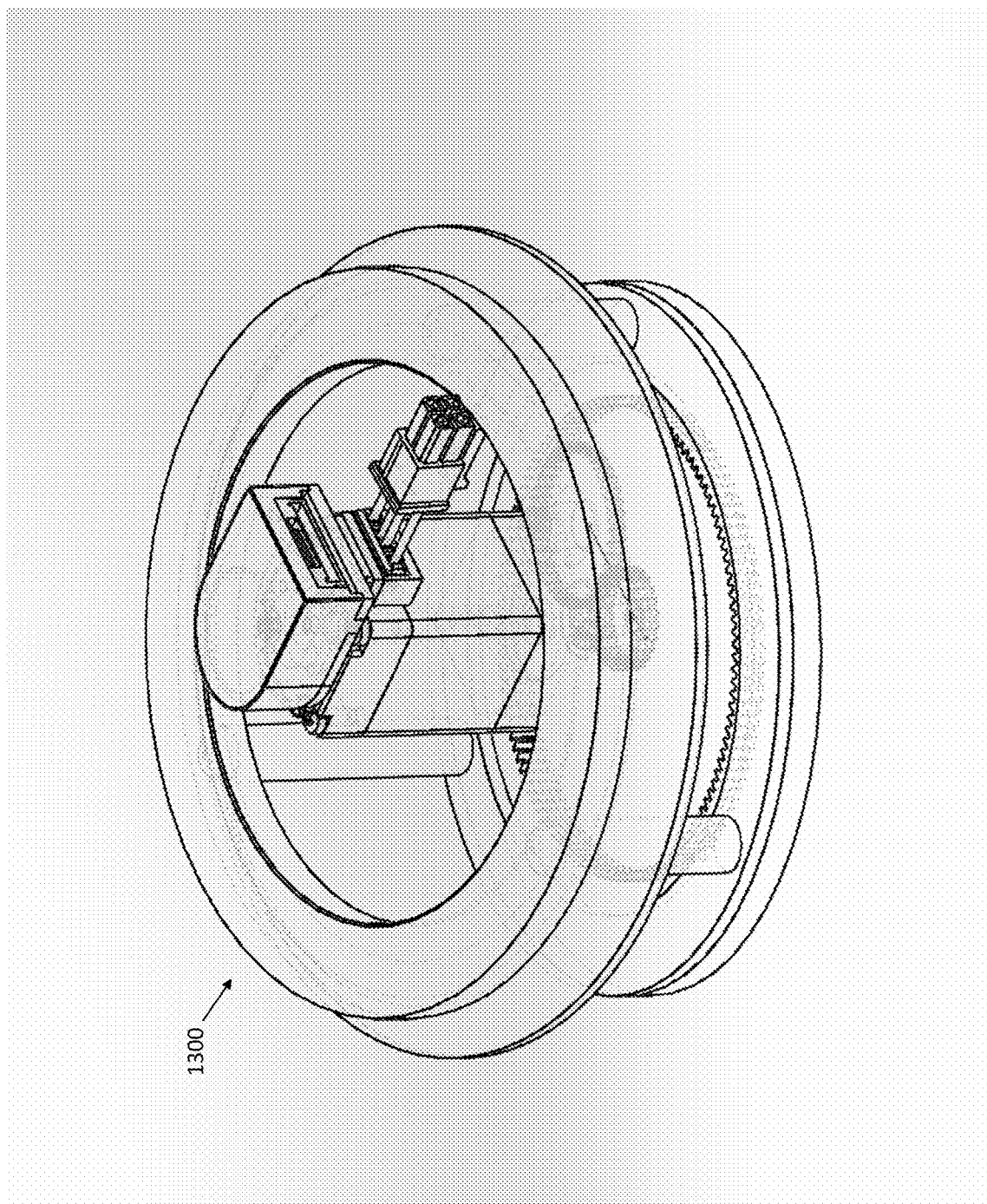
FIGS. 13A-13B illustrate a motor assembly according to embodiments of the present disclosure.
Figure 13B:
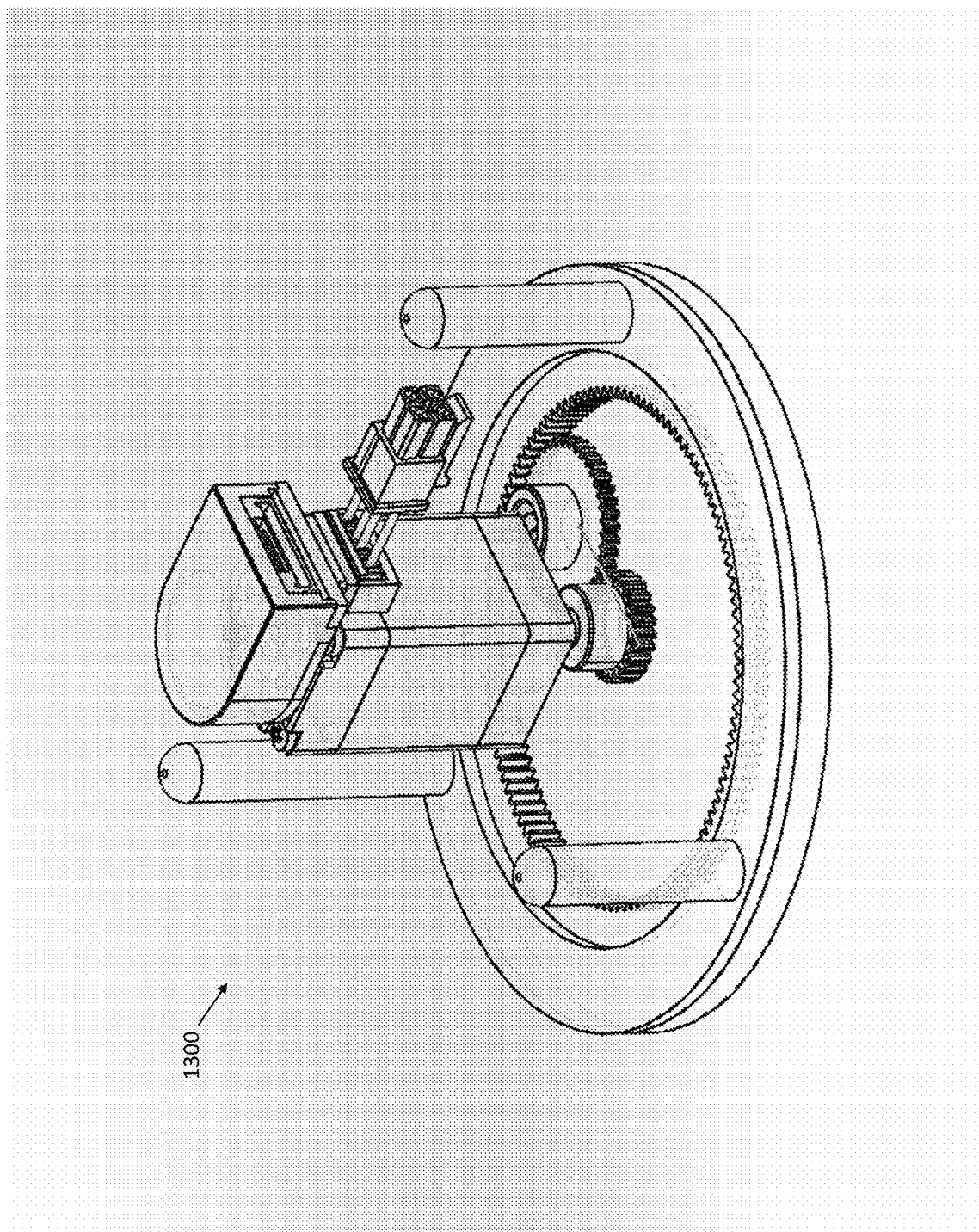

FIGS. 12A-12C illustrates a motor assembly 1200 according to embodiments of the present disclosure. FIGS. 13A-13B illustrates a motor assembly 1300 according to embodiments of the present disclosure.

Figure 14A:
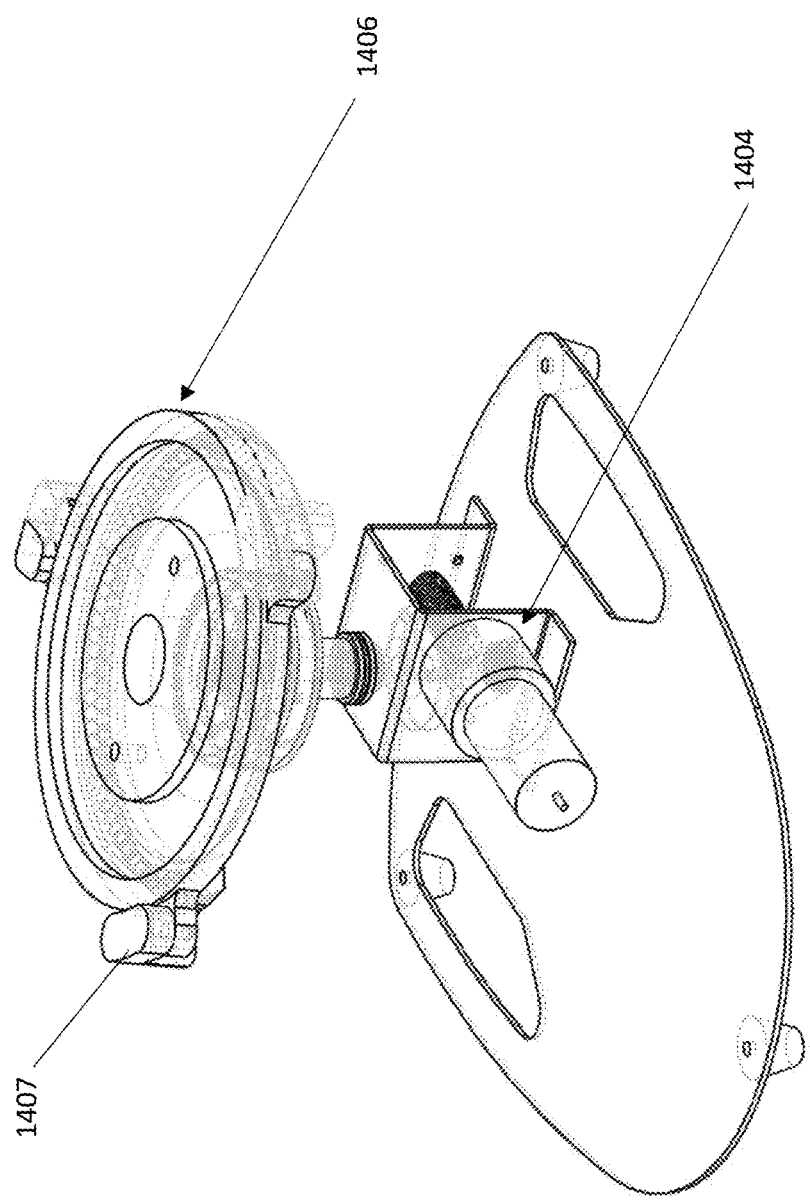
FIGS. 14A-14B illustrate a motor assembly and torus holder according to embodiments of the present disclosure.
Figure 14B:
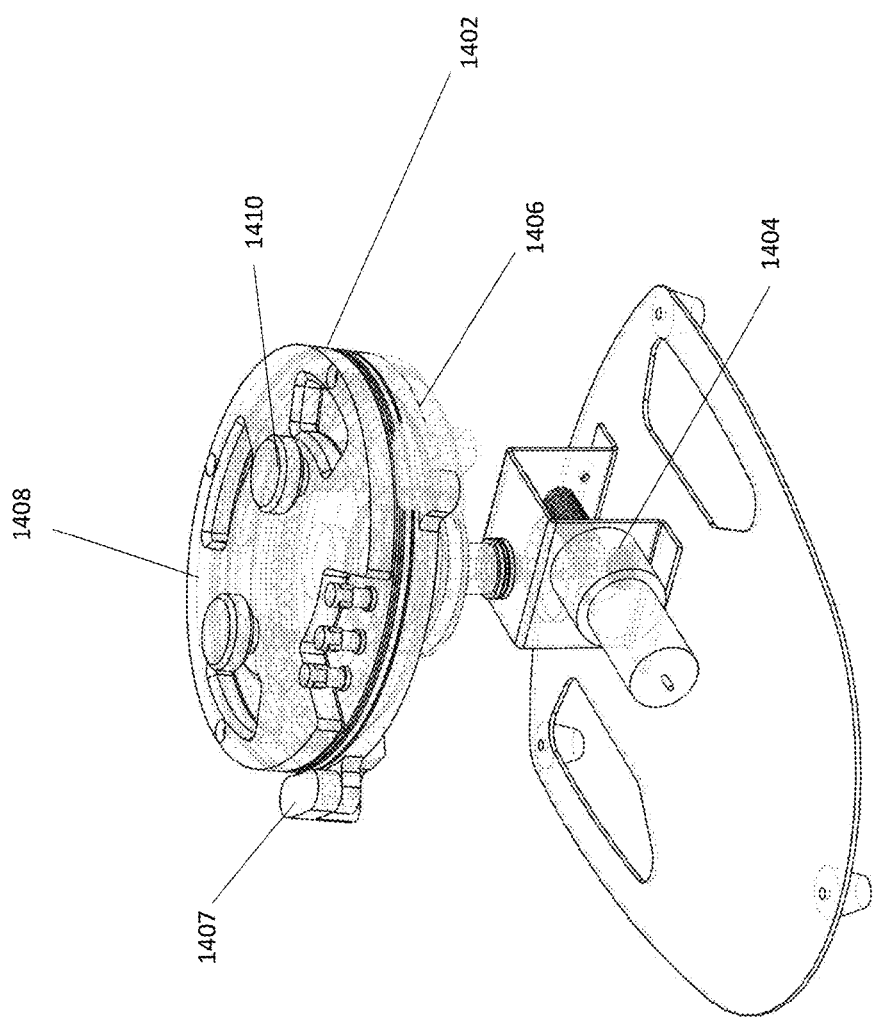

FIGS. 14A-14B illustrates a motor assembly 1404 and torus holder 1406 according to embodiments of the present disclosure. As shown in FIG. 14A, the motor assembly 1404 is disposed on a flat mount having legs (e.g., rubber) to reduce vibrations to the supporting surface. The motor assembly 1404 may be connected to a dock (e.g., an intelligent dock) to thereby program a predetermined rotation process. The torus holder 1406 may be formed such that the holder 1406 has a conforming interface with a torus reactor assembly of the present disclosure. A torus reactor assembly (not shown) may be placed on the holder 1406 and releasably coupled to the holder 1406 via one or more location features 1407 (e.g., clamps). In various embodiments, a magnetic ring may be coupled to the holder 1406 (e.g., on the outer circumference of the bottom of holder 1406). FIG. 14B shows a consumable torus reactor 1402 with a lid 1408 and auxiliary lid components 1410 fitted to the rotation system (e.g., a 3D rocker).

Figure 15A:
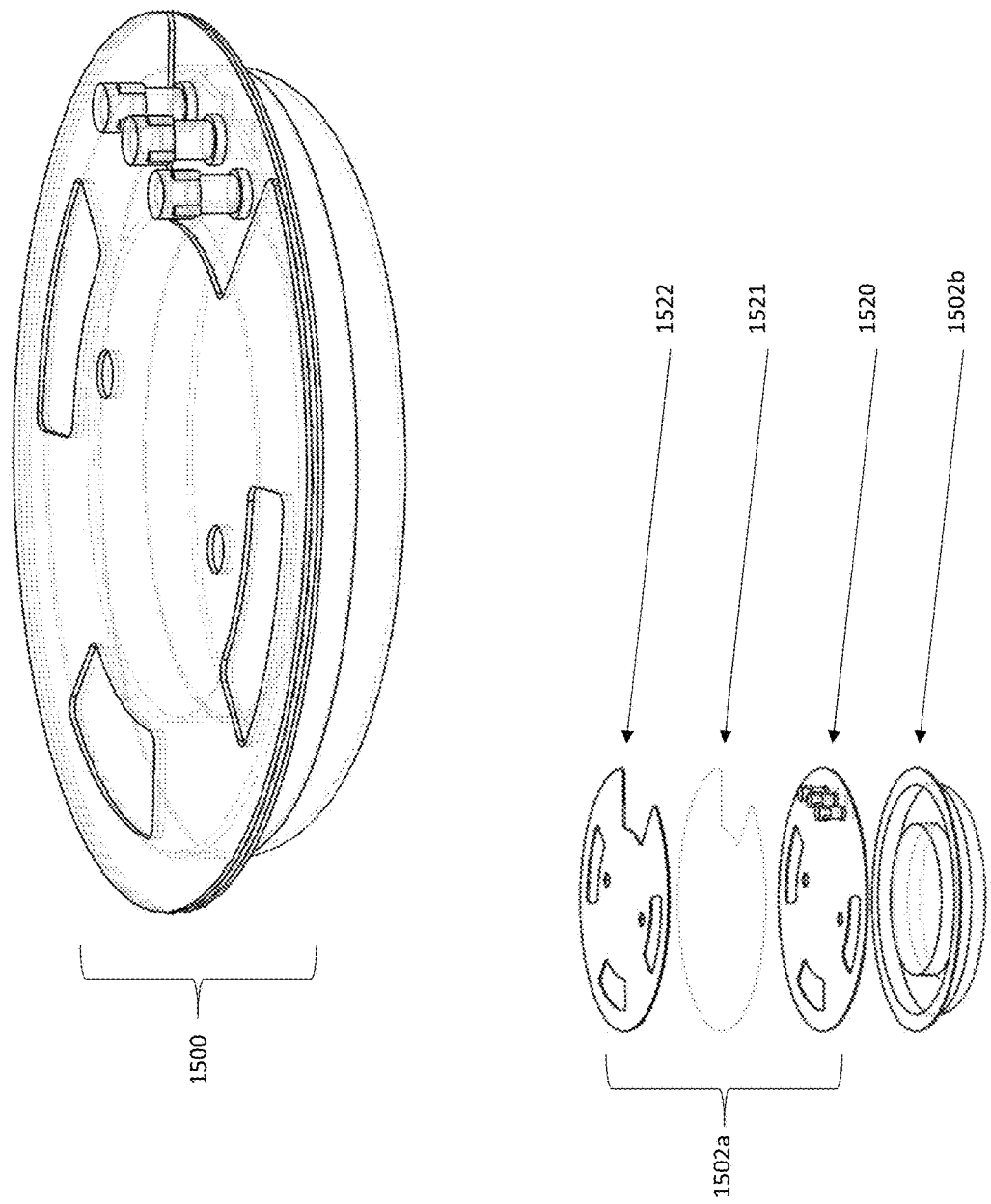
FIGS. 15A-15C illustrate a torus chamber assembly according to embodiments of the present disclosure.
Figure 15B:
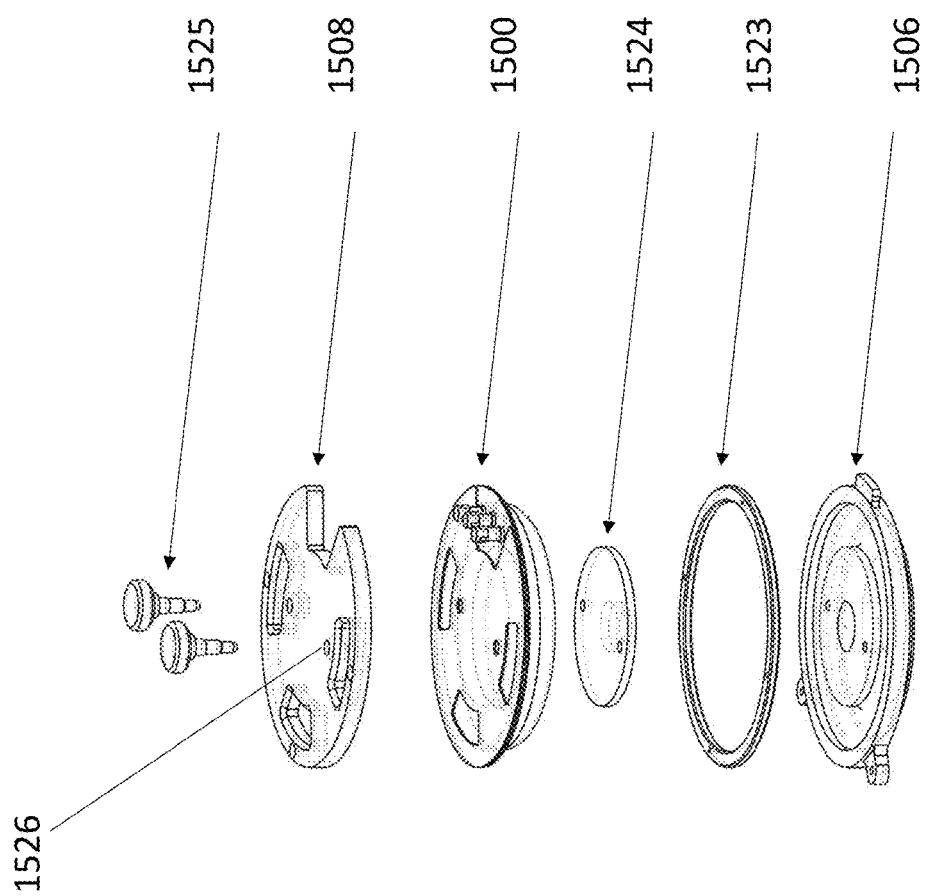
Figure 15C:
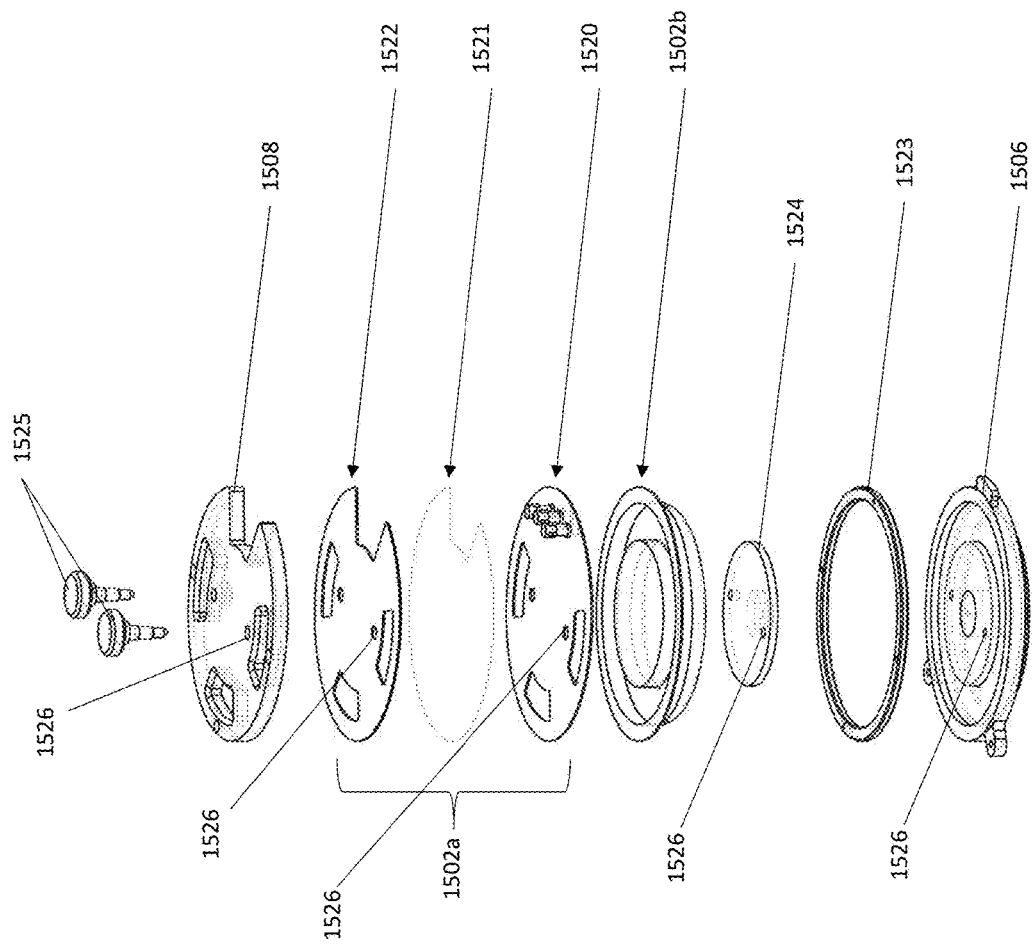

FIGS. 15A-15C illustrates a torus chamber assembly 1500 according to embodiments of the present disclosure. In particular, the torus chamber assembly 1502 may include a lower portion (e.g., a semi-toroidal chamber) 1502*b* as described in more detail above. In various embodiments, the torus chamber assembly 1500 further includes an upper portion (e.g., a lid) 1502*a*. In various embodiments, the upper portion 1502*a* may include two or more components that together form the upper portion 1502*a*. In various embodiments, the upper portion 1502*a* may include a lid lower layer 1520 that includes one or more ports and/or access channels to the inner chamber of the lower portion 1502*b*. In various embodiments, the upper portion 1502*a* may include a filter layer 1521 that may include a filter and/or gas exchange material. In various embodiments, the filter layer 1521 may be a sheet that is sandwiched between the layers of the upper portion 1502*a*. In various embodiments, the filter layer 1521 may include one or more discrete areas or patches of filter and/or gas exchange material. In various embodiments, the upper portion 1502*a* may further include a lid top layer 1522 that is affixed to the lid lower layer 1520 to thereby hold the filter layer 1521 in place and provide access to the filter layer 1521 so that a user may replace the filter layer 1521 as needed.

As shown in FIG. 15B-15C, the system may include various auxiliary components in addition to the torus reactor assembly 1500 and the holder 1506. In particular, the system may further include a lid lower outer ring 1523 used to secure and seal the consumable torus assembly along the outer circumference of the torus assembly. The system may further include a lid lower center 1524 used to secure and seal the consumable torus assembly and provide material to fasten the lid cover 1508. In various embodiments, the system may further include one or more fasteners 1525 (e.g., thumb screws) configured to releasably affix all of the components together. The fasteners 1525 may be inserted into holes 1526 formed in two or more of the components (that may be threaded or not threaded) as shown in FIG. 15B.

Figure 16A:
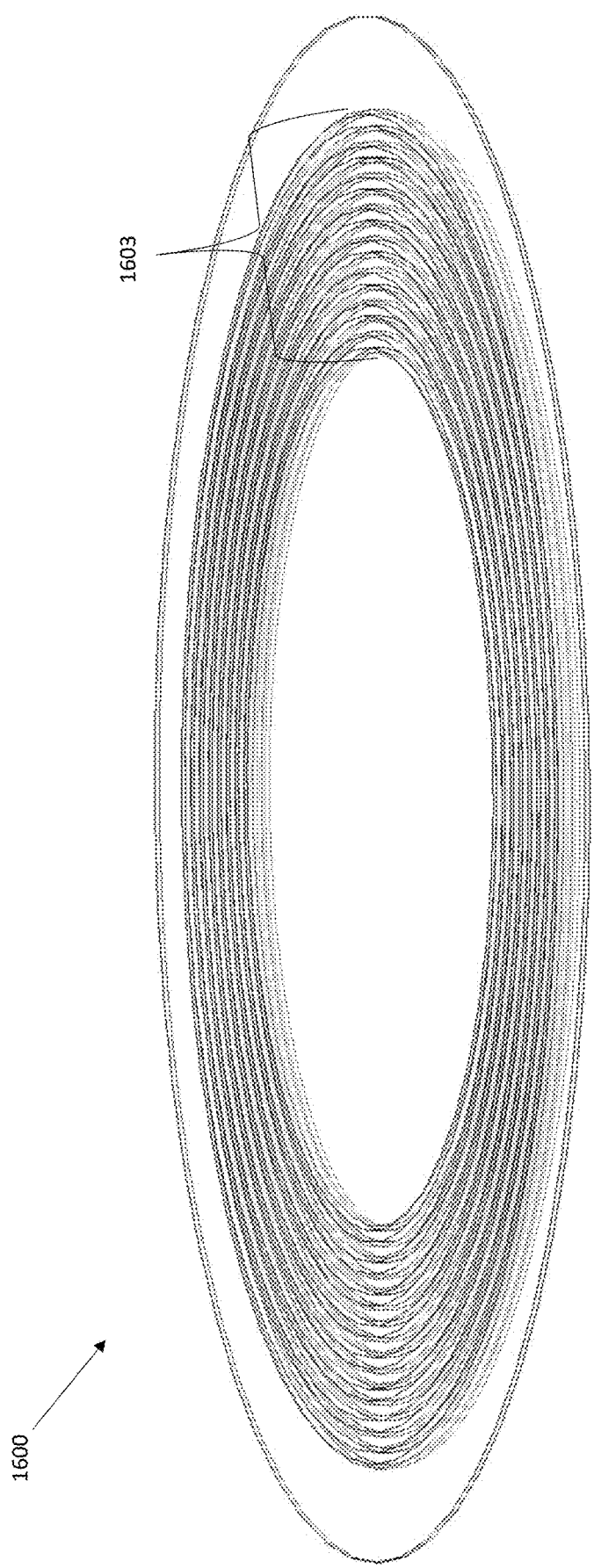
FIGS. 16A-16B illustrate a torus chamber having multiple channels according to embodiments of the present disclosure.
Figure 16B:
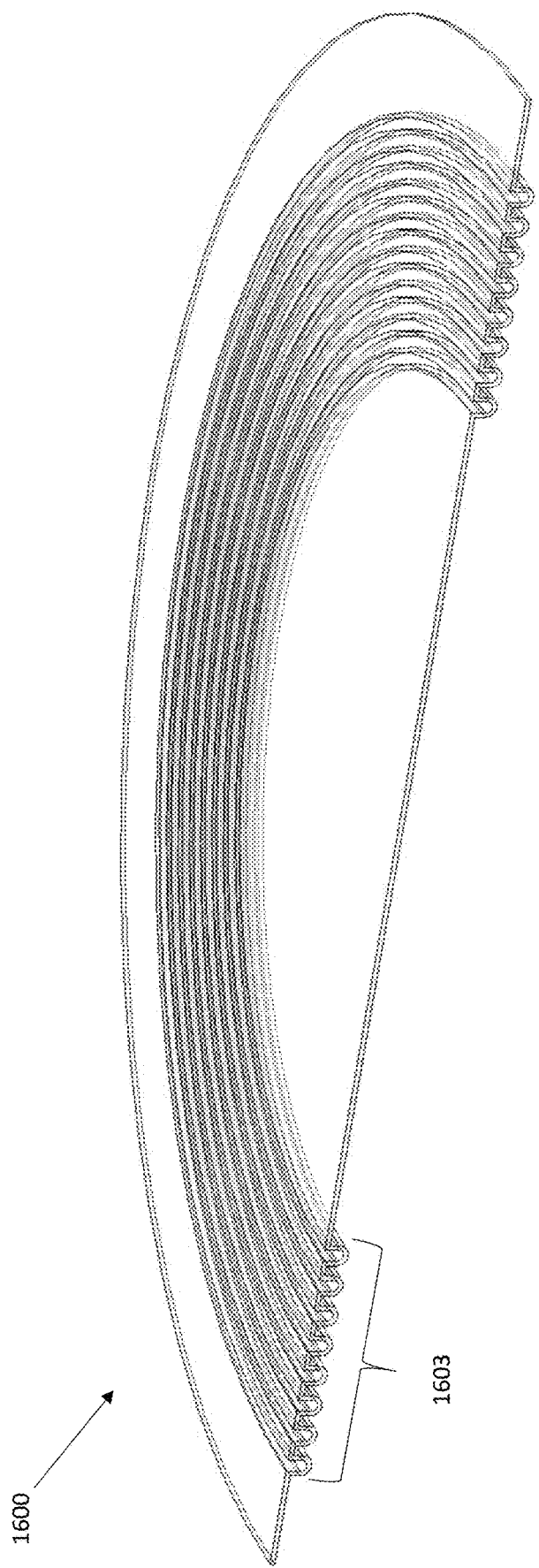

FIGS. 16A-16B illustrate a torus chamber 1600 having multiple channels 1603 according to embodiments of the present disclosure. In various embodiments, a torus chamber 1600 may include any suitable number of channels 1603, and is not limited to the number of channels shown in the figures. For example, the torus chamber 1600 may include eight (8) channels, as shown in FIGS. 16A-16B. Each channel may receive a separate suspension/solution of target material and non-target material(s) for isolation of the target material as described in more detail above. In various embodiments, each channel 1603 is in fluid communication with a designated opening in the lid to prevent cross-contamination of samples.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system for isolation of one or more target materials disposed within a fluid, the system comprising:
   an isolation assembly comprising:
   a housing having an upper portion and a lower potion together defining an inner chamber configured to receive the fluid, the inner chamber comprising a semi-toroidal ring shape, the semi-toroidal ring shape defining a longitudinal axis;
   one or more fluidic connections to the inner chamber; and
   an isolation material disposed within the inner chamber, the isolation material selected from the group consisting of a polymer wool and magnetic particles;
   a platform configured to fit at least a portion of the housing and releasably couple the housing; and
   a motor coupled to the platform operable to move the isolation assembly upon activation;
   wherein, when the motor is activated, the platform is configured to rotate the isolation assembly at an adjustable angle and an adjustable speed such that the fluid contained within the internal chamber travels around the semi-toroidal ring shape in a single direction to thereby optimize mixing, gas exchange, and/or isolation of the one or more target materials and reduce cellular stress during motion.

2. The system of claim 1, further comprising a magnetic ring releasably coupled to the housing, the magnetic ring comprising one or more permanent magnets.

3. The system of claim 2 wherein the one or more permanent magnets comprise a Halbach array, and are adjustable to point the Halbach array towards or away from the inner chamber.

4. The system of claim 2, wherein the magnetic ring extends around about 25% to about 80% of a circumference of the housing.

5. The system of claim 1, wherein the polymer wool comprises a polyamide wool.

6. The system of claim 1, further comprising one or more frit disposed in the inner chamber configured to position the one or more target materials within the fluid.

7. The system of claim 6, wherein the one or more frit comprises one or more slits.

8. The system of claim 6, wherein the one or more frit separates the inner chamber into two or more zones to thereby isolate material in each zone from one another.

9. The system of claim 1, wherein the inner chamber comprises a plurality of channels.

10. The system of claim 1, wherein, when the motor is activated, the isolation assembly rotates about the longitudinal axis.

11. The system of claim 1, further comprising an environmentally-controlled chamber, wherein the assembly is disposed within the environmentally-controlled chamber.

12. A method comprising:
   providing the system of claim 1, wherein the fluid further comprises one or more non-target materials;
   loading the fluid into the inner chamber via at least one of the one or more fluidic connections;
   engaging the isolation assembly with the platform;
   activating the motor to rotate the isolation assembly about the longitudinal axis at a selected angle and speed thereby causing either the one or more target materials or the one or more non-target materials to interact with the isolation material; and
   extracting either the one or more target materials or the one or more non-target materials from the isolation assembly that did not interact with the isolation material thereby isolating the one or more target materials or the one or more non-target materials within the isolation assembly.

13. The method of claim 12, further comprising adjusting the angle of the platform.

14. The method of claim 12, wherein the speed is adjustable up to 200 Hz.

15. The method of claim 12, wherein the one or more target materials is are selected from the group consisting of: T cells, B cells, natural killer cells, monocytes, Peripheral Blood Mononuclear Cells (PBMCs), apheresis materials, whole blood, a cultured material, a nucleic acid, a protein, an enzyme, an antibody, and an antigen.

16. The method of claim 12, further comprising washing the one or more target materials.

17. The method of claim 16, wherein the one or more target materials comprises target cells, the method further comprising:
   introducing one or more regents into the inner chamber to activate the target cells; and after washing, transducing the target cells by introducing DNA via a virus or viral vector.

18. The method of claim 17, further comprising expanding the target cells to a predetermined concentration after activating and transducing the target cells.

19. The method of claim 18, wherein expanding the target cells comprises supplying one or more gases to the inner chamber via at least one of the one or more fluidic connections, the one or more gases comprising carbon dioxide.

20. The method of claim 18, wherein expanding the target cells further comprises adjusting the angle and/or the speed.

21. The system of claim 1, further comprising a sensor and a programmable control configured to adjust the angle and/or the speed in real time.

* * * * *